US011138201B2

(12) United States Patent
Srinivasa et al.

(10) Patent No.: US 11,138,201 B2
(45) Date of Patent: Oct. 5, 2021

(54) SYSTEM AND METHOD FOR INTEGRATING DATA FOR PRECISION MEDICINE

(71) Applicant: OMICS DATA AUTOMATION, INC., Beaverton, OR (US)

(72) Inventors: Ganapati Srinivasa, Portland, OR (US); Melvin Lathara, Portland, OR (US); Brian Hill, Cornelius, OR (US); Jaclyn Smith, Vida, OR (US); Nalini Ganapati, Portland, OR (US); Hollis Wright, Portland, OR (US)

(73) Assignee: OMICS DATA AUTOMATION, INC., Beaverton, OR (US)

(*) Notice: Subject to any disclaimer, the term of this patent is extended or adjusted under 35 U.S.C. 154(b) by 350 days.

(21) Appl. No.: 16/205,081

(22) Filed: Nov. 29, 2018

(65) Prior Publication Data

US 2019/0163679 A1 May 30, 2019

Related U.S. Application Data

(60) Provisional application No. 62/592,164, filed on Nov. 29, 2017.

(51) Int. Cl.
*G06F 16/2455* (2019.01)
*G16H 10/60* (2018.01)
*G06F 16/248* (2019.01)
*G06F 16/2458* (2019.01)
*G06F 16/25* (2019.01)

(52) U.S. Cl.
CPC ........ *G06F 16/2456* (2019.01); *G06F 16/248* (2019.01); *G06F 16/2465* (2019.01); *G06F 16/258* (2019.01); *G16H 10/60* (2018.01)

(58) Field of Classification Search
None
See application file for complete search history.

(56) References Cited

U.S. PATENT DOCUMENTS

| 2007/0106754 A1* | 5/2007 | Moore | G06F 16/958 709/217 |
| 2007/0130206 A1* | 6/2007 | Zhou | G16H 50/20 |
| 2007/0294110 A1* | 12/2007 | Settimi | G06Q 10/10 705/3 |
| 2007/0294111 A1* | 12/2007 | Settimi | G16H 10/20 705/3 |
| 2008/0040151 A1* | 2/2008 | Moore | G16H 10/60 705/2 |

(Continued)

OTHER PUBLICATIONS

"The Open Microscopy Environment," Open Microscopy Website, Available Online at https://www.openmicroscopy.org, Available as Early as Apr. 28, 2001, 4 pages.

(Continued)

*Primary Examiner* — Richard L Bowen
(74) *Attorney, Agent, or Firm* — McCoy Russell LLP

(57) ABSTRACT

Methods and systems are provided for a platform and language agnostic method for generating inter- and intra-data type aggregations of heterogenous disparate data upon which various operations can be performed without altering the structure of the query or resulting distributed data set representation to account for which specific data sources are included in the query.

20 Claims, 16 Drawing Sheets

(56) References Cited

U.S. PATENT DOCUMENTS

| | | | | |
|---|---|---|---|---|
| 2015/0331995 | A1* | 11/2015 | Zhao | G16H 30/20 |
| | | | | 705/2 |
| 2018/0039737 | A1* | 2/2018 | Dempers | G06F 19/00 |
| 2019/0180862 | A1* | 6/2019 | Wisser | G16H 80/00 |
| 2020/0234825 | A1* | 7/2020 | Dobson | G16H 80/00 |

OTHER PUBLICATIONS

Mell, P. et al., "The NIST Definition of Cloud Computing," National Institute of Standards and Technology, Special Publication 800-145, Sep. 2011, 7 pages.

Zaharia, M., "An Architecture for Fast and General Data Processing on Large Clusters," Doctor of Philosophy in Computer Science Dissertation, University of California, Berkeley, Feb. 3, 2014, 128 pages.

"Should I analyze my samples alone or together?," Broad Institute Website, Available Online at https://software.broadinstitute.org/gatk/documentation/article.php?id=4150, May 9, 2014, 3 pages.

"Spark SQL, DataFrames and Datasets Guide," Apache Spark Website, Available Online at http://spark.apache.org/docs/latest/sql-programming-guide.html, Available as Early as Jun. 8, 2014, 2 pages.

"i2b2 'How to'—Installation, Startup and Extending its Functionality," i2b2 Website, Available Online at https://www.i2b2.org/software/tutorial.html, Nov. 16, 2014, 2 pages.

"ExAC project pins down rare gene variants," Nature Magazine, vol. 536, No. 249, Aug. 17, 2016, 3 pages.

"Genome Analysis Toolkit—Variant Discovery in High-Throughput Sequencing Data," Broad Institute Website, Available Online at https://software.broadinstitute.org/gatk/, Available as Early as Oct. 10, 2016, 2 pages.

"Welcome to the LabKey Support Portal," LabKey Website, Available Online at https://www.labkey.org/home/project-begin.view?, Available as Early as Feb. 20, 2016, 1 page.

"Broad Institute Teams Up With Intel to Integrate Genomic Data From Diverse Sources and Enhance Genomic Data Analytic Capabilities," Broad Institute Website, Available Online at https://www.broadinstitute.org/news/broad-institute-teams-intel-integrate-genomic-data-diverse-sources-and-enhance-genomic-data, Nov. 17, 2016, 3 pages.

Papadopoulos, S. et al., "The TileDB Array Data Storage Manager," Proceedings of the VLDB Endowment, vol. 10, No. 4, Dec. 2016, Munich, Germany, 12 pages.

Prabhakaran, A. et al., "Infrastructure for Deploying GATK Best Practices Pipeline," Intel Website, Available Online at https://www.intel.com/content/dam/www/public/us/en/documents/white-papers/deploying-gatk-best-practices-paper.pdf, Available as Early as Feb. 25, 2017, 28 pages.

"TileDB," TileDB Wesbite, Available Online at https://tiledb.io/, Available as Early as Oct. 20, 2017, 4 pages.

"What are the GATK Best Practices?," Broad Institute Website, Available Online at https://software.broadinstitute.org/gatk/best-practices/, Jan. 9, 2018, 3 pages.

"OQL—Onco Query Language," CBioPortal Website, Available Online at http://www.cbioportal.org/oql, Retrieved on Feb. 27, 2019, 9 pages.

* cited by examiner

FIG. 5  Below are the patient sets extracted.

FIG. 7

```
class Gentoype{
  sampleName: String,
  geno: List[String],
  call: Int
} class Consequence{
  variant_allele: String,
  consequence_terms: List[String],
  biotype: String,
  impact: String,
  gene_id: String,
  hgnc_id: String,
  transcript_id: String,
  gene_symbol: String
} class Annotation{
  allele_string: String,
  assembly_name: String,
  end: Long,
  id: String,
  input: String,
  consequences: List[Consequence],
  most_severe_consequence: String,
  seq_region_name: String,
  start: Long,
  strand: Long,
} class Variant{
  contig: String,
  start: Int,
  ref: String,
  alts: List[String],
  genotypes: List[Genotype],
  annots: List[Annotation]
}
```

SYSTEM AND METHOD FOR INTEGRATING DATA FOR PRECISION MEDICINE

CROSS REFERENCE TO RELATED APPLICATIONS

The present application claims priority to U.S. Provisional Application No. 62/592,164, entitled "SYSTEM AND METHOD FOR INTEGRATING DATA FOR PRECISION MEDICINE", and filed on Nov. 29, 2017. The entire contents of the above-listed application are hereby incorporated by reference for all purposes.

FIELD OF TECHNOLOGY

The present description relates generally to systems and methods for accessing, transforming, integrating, pooling, and analyzing heterogeneous forms of siloed data.

BACKGROUND

Health care data is generally stored in a variety of forms in a variety of locations. Patient information, test results, imaging data, diagnostic data, pharmacological information, electronic health records, and the like are frequently produced and stored in one or more proprietary formats as text, images, video, multimedia, and the like. Records may be electronically stored in disparate locations in various hospital departments, doctor's offices, and with outside providers in a variety of structured, semi-structured, and unstructured formats, making collection and analysis of an entire individual record, let alone collections of records from multiple individuals, difficult, if not impossible.

Precision medicine takes into account various types of health-related data in order to allow doctors and researchers to tailor treatment and prevention strategies to an individual patient. Such an approach is in contrast to traditional medical treatment in which symptomatic treatment and prevention strategies developed for a theoretical average person are applied to everyone. By taking into consideration individual variability in genes, molecular and cellular analysis, environment, and lifestyle, precision medicine allows medical practitioners to predict which treatments and strategies will be effective in specific groups of people, which may increase the likelihood that any one treatment or groups of treatments may be effective for an individual patient. However, in order to exploit the promise of precision medicine, health care data needs to be accessible.

In order to tailor treatment and prevention strategies to an individual patient, it may be useful to accumulate medical data and treatment outcomes from subpopulations (e.g. cohorts) of patients with similar or the same health profiles. Generation of such cohorts may involve identifying a set of individuals with similar symptoms, genetic profiles, and other relevant medical data obtained from electronic health records (EHRs), genomic sequence data, pathology tissue images, magnetic resonance imaging (MRI) data, ultrasound results, lab work, etc. Information from such subpopulations may be used to assist in diagnosis and identification of effective treatment plans for an individual patient who matches that subpopulation. For example, a comparison of treatment of patients in the cohort may result in the identification of the most effective treatment for individuals in that subpopulation.

As many diseases do not have a simple diagnostic test, diagnosis may rely on interpretation of different types of medical data in different forms, and thus identifying subpopulations of patients with similar or the same health profiles can be challenging. Further, currently, such data records are kept in data silos in which information systems or subsystems are incapable of reciprocal operation with others that are, or should be, related, making data sharing and compilation a time consuming, manual exercise. These disparate storage systems can make it challenging to deduce cross-correlations and can prevent generalized applications of machine learning to the collective data. Further, each silo may have different security and access requirements increasing the level of complexity and difficulty in accessing even individual records.

As an example, a desired cohort may comprise a cohort of patients within a particular age group (e.g., 20-30 years old), with a particular diagnosis. A clinician or researcher may seek to evaluate the effectiveness of particular treatments in such patients who have a specific genetic mutation or other relevant biomarker(s), or may seek to identify genetic mutations or other biomarker(s) that could potentially impact the effectiveness of treatment in such patients. In order to identify the desired cohort, a health professional may currently undergo an onerous process of identifying the desired pieces of data to form a relevant set of patients, identifying the location of the appropriate data source, and locating the desired information in one or more traditional relational data sources or multi-dimensional records. Each piece of the desired information may be stored in different data sources, in different formats, and at different locations with different access and searching requirements, making the generation and analysis of such a desired cohort challenging and time consuming.

Currently, a health professional must identify, access and open each of the separate data sources (e.g. opens EHR, imaging, pathology, and genomic sequence data sources), identify how and where the desired information is stored (e.g., which data source, what file format, how the data source stores and organizes information, what specific fields provide the desired information, how to obtain information from a particular source) and then perform the desired operations serially to identify the individuals who may be used to create the desired cohort. Further, many databases require a user to enter requests using imperative queries which require an extensive knowledge of the language and technical understanding of physical implementation details prior to usage.

Once such a desired cohort has been identified, the various treatment options that each individual within the cohort has received may be identified, and treatment outcomes analyzed. Treatment protocols and outcomes may be recorded as a series of individual patient visits over extended periods of time with their own accompanying imaging, pathology and physician notes, stored in different formats in different locations, complicating efforts to obtain and analyze data. In such an approach, computational run time may grow exponentially as more data are incorporated into criteria for generation of such a desired cohort. Further, for many diseases and conditions, there is no single diagnostic test and even the initial diagnosis requires compilation and analysis of medical records from individual data silos which may not be easily accessible to a medical practitioner.

As a simplified example, consider a patient with a diagnosis of breast cancer. Diagnostic documents include the patient's medical history, family history, imaging, pathology, and treatments. Pathology may include size, type, and grade, hormone receptor status, HER2 receptor status, molecular subtype, histology images, and genetic analysis of the tumor. Each of these types of data may be stored in different formats in different locations. Treatment options may include surgery, radiation therapy, chemotherapy, hormone therapy, and target therapy, all of which can have inherent risks and side effects. Identifying the most effective type of treatment or combination of treatments for a particular disease requires understanding the success of treatment options for similarly situated patients. Taking into account all of the above-mentioned variables in order to identify similarly situated patients and most appropriate treatment options is current challenging for the reasons set forth above.

Thus, realization of the potential promise of precision medicine relies on accessing and analyzing large, multidimensional datasets. The isolation of biomedical data in separate silos makes this challenging. For example, even after particular desired data is extracted from data silos, such data may be incompatible for cross-comparison due to the file format, technical architecture, application architecture, or data architecture. Traditional data structures such as data warehouses that rely on specific data architectures are not designed to scale with the amount and number of different types of data that form biomedical resources. Thus, a scalable approach that enables greater facilitation of data sharing between silos, while reducing costs associated with processing the information stored in individual silos, is needed.

SUMMARY

Systems and methods described herein disclose techniques in the area of precision medicine. Such systems and methods may be used to access, transform, integrate, and analyze biomedical data for a plurality of individuals from a plurality of data sources for a plurality of uses. Exemplary types of biomedical data include, but are not limited to, symptoms and recorded observations, genetic sequencing information, gene mutations, imaging data, pharmacological data, blood work, or other tests. Such information may be used, for example, to identify diagnostic criteria, diagnose disease, evaluate treatment protocols, prescribe potential treatment protocols, identify treatment targets, and the like. In some aspects, such information may be used to predict, diagnose, and treat individuals with similar lifestyle, phenotypic, genotypic, disease, or other health related profiles.

Currently, biomedical data is stored in one or more places on one or more computers on one or more networks. Frequently, such data is isolated in a data silo, a repository of information incapable of reciprocal operation with others that are, or should be, related and that is generally sequestered within a system or subsystem. Within data silos, each type of data or each collection of data may be isolated behind one or more different security protocols in one or more different formats. Even within a silo, data may be stored in different places. For example, Genomics DB is a columnar-based array data management system that can be heavily distributed. A single Genomics DB instance can comprise of many partitions organized across multiple machines. Further, many testing methods, results, or medical data entry systems use proprietary software, or are outsourced to third parties, leading to data that is difficult to access and aggregate. The amount of data available for any one individual, let alone a population of individuals, creates difficulties in reviewing and analyzing the data in order to obtain meaningful and useful information about an individual, subpopulation, disease, or treatment protocol.

Described herein are systems and methods for accessing and retrieving biomedical data isolated in silos, creating data source objects, and, from the data source objects, creating data abstraction objects and data pools (e.g. multidimensional data pools) which may comprise one or more data source objects. The resulting data abstraction objects and data pools may be used to integrate and analyze medical data from one or more individuals or cohorts, obtain diagnostic criteria, evaluate treatment protocols, and identify treatment targets, among other uses.

Data silos containing biomedical data of interest may be located in one or more partitions within a computer, on one or more computers as sets of records or in a distributed manner, through one or more networks, or a combination thereof. In some embodiments, each type of biomedical data is located in a different data silo. Such data may be stored in the same or different formats including, but not limited to, ASCII, JPEG, GIF, diagnostic imaging, FASTA, BED, 2 bit, GTF2, GFF3, PSL, BigBED, BedGraph, wiggle, BigWig, bowtie, SAM, PSL, BAM, HL7, X12, CCR, CCD, C32, CCDA, DICOM, TIFF, PNG, compressed files, ISO, SDI, database files, flat files, PDF, formatted text, plain text, and XML, or any other type of format in which medical or other patient related data may be stored.

The biomedical data stored in data silo(s) may belong to one or more patients and may be from one or more points in time, for example one or more doctor visits or one or more set(s) of lab results. In some aspects, the methods and systems described herein retrieve individual biomedical data from a series of data silos. In other aspects, the methods and systems described herein may retrieve data for groups of individuals defined along one or more dimensions.

In the context of the present disclosure, a query entered into the system by a user may be defined by, formatted according to, mappable to, have one or more parameters defined by and/or selected in accordance with, able to be parsed by, a data integration specification that supports comprehensive declarative queries over disparate, heterogeneous data sources through the use of a data integration schema. Such queries may be parsed into one or more query segments appropriate for a specific data source. The data integration schema may be stored on the same or a different device than the device onto which the query was entered. Specifically, the comprehensive data integration specification may enable a user to pose cohesive queries over siloed data sources in a unified analysis environment. The query may be mapped to the data integration schema which may be platform/language agnostic and compatible with distributed computing technologies (e.g., MPI, Spark) and may include configurations for each of the data sources to enable aggregation and processing of the disparate data.

Each data source (e.g., GenomicsDB for genomic variant data, an EHR system with clinical data, or a relational data source with clinical trial metadata) may have a specific transformation and loading process which may support a representation of heterogeneous data in distributed data set structures specified by the data integration schema. The access of data from each of the individual data sources may be via specialized transformations, partitioning, and loading process(es) (e.g., data source-specific schema) to load data constrained by the data integration schema as set by the particular query, and to function as an integrated data abstraction object for computation, where a data abstraction object comprises one or more data set(s) distributed across a plurality of machines. In the context of this disclosure, each data source-specific schema may comprise a description of an individual data source with a supported format and methods to translate data extracted from the individual data sources into a representation backed by the data integration schema in the comprehensive data integration specification. While such translation may occur using any means generally used, in some aspects it occurs via primary and foreign keys. The translation from a specialized representation as specified by the data source-specific schema, to global representation in the context of the data integration schema, may be predefined and may be automatically configured for any particular instances of a data source specific-schema and data integration schema pair, but may also in some examples be extended to accommodate changes in the data integration schema to enable support for new types of data sources.

In general, the data integration schema may also define how a record from a data source of a specific type is represented as the data abstraction object(s). Such representation may be based on common access/analysis patters for the particular data type(s). For example, genomic variant data queried from two data sources (source A and source B, for example) may be returned to a user in a same standardized format defined by the data integration schema. Such a standardized format may be based on a common analysis of the data type as well as any operations required to support aggregate queries, as discussed in further detail below.

Data may be queried from a particular data source(s) and transformed based on the data source-specific schema for that particular data source, to participate as a distributed data source object. In some aspects, the data may be filtered to remove noise or other unwanted data and then used to create one or more data source object(s). The filter for the data may be the same or different depending on the type of data being filtered and/or the information of interest. The data source-specific schema may be generated and the translation to the data integration schema may occur in an automated fashion based upon one or more integrity constraints, such as foreign keys, and the data integration schema, though it may be understood that individual data source-specific schema may be manually modified as desired for any specific application. The data source-specific schema may also support security and access control features if/when implemented for the particular data source.

In some aspects, the data source object may comprise a distributed data set loaded from a data source and associated with a data source specific schema. In some examples, the data source objects may be combined in a data pool, also referred to herein as a multi-dimensional pool or multidimensional data pool. In other words, the data pool or multi-dimensional pool may be composed of one or more data source object(s). The data abstraction object or comprehensive data integration specification may comprise a logical view of the data source object(s) as defined by a data integration schema. Abstraction, in general, is the process of transforming characteristics from something in order to reduce it to a set of essential characteristics. The data integration schema may track associations and overlaps between data sources by maintaining one or more integrity constraint(s) within and among such data sources. A granularity of integrity constraints (e.g., foreign keys) for each of the data source objects (which may comprise heterogeneous objects) may be defined based on analytical pipelines as specified by users. Thus, the data integration schema or mapping database may be optimized to maintain those source relationships of interest. Such relationships may be readily altered and extended as particular needs of the system evolve to include additional data types and analysis pipelines.

In conducting a query operation on a set of siloed data sets, a query posed by a user is transformed into a cohesive query generated in terms of the data integration schema. The cohesive query may include or contain query segments specific to each relevant data source such that the query segments are posed to one or more data sources/silos, data is extracted from these sources according to each source's data source-specific schema and loaded into the comprehensive data integration specification defined by the data integration schema. Data may be extracted for one or more individuals from one or more data sources serially, in parallel, and/or in a distributed fashion. The extracted data in data integration schema format is represented as one or more distributed data sets. By leveraging the integrity constraints and the data integration schema, distributed data sets are joined based on the needs of the user-defined analysis into the results of the cohesive query. This mechanism allows for support in both joining data sets from disparate data sources representing the same type of data (e.g., variant information from VCF files and a GenomicsDB instance, or two GenomicsDB instances located at different institutions) and more complex aggregate operations that integrate disparate data types as defined by the data integration schema identified by the user.

Once the data is retrieved and transformed to pools of distributed data source objects, various types of analysis may be performed on the pools of data. For example, a user may want to join genomic variant data and clinical data based on a patient identifier (an integrity constraint defined in the data integration schema). After joining, the result may be grouped by clinical label and a genomic aggregate calculation, such as genotype distribution, as calculated for each of the genomic variants for each clinical label category. Other examples of the types of various analyses which may be performed on the pools of data may include but are not limited to genome wide association studies (GWAS), subset selection for analysis based on multiple data sources, statistical analyses involving multiple data sources (e.g. deep learning across multiple data sources). As further examples, automated cell counting, ethnicity projection, etc., may comprise examples of deep learning/machine learning analyses which may be performed on the pools of data.

Discussed herein, the data integration schema provides a platform and language-agnostic method for generating inter- and intra-data type aggregations that permit users to define operations on the data in terms of the data integration schema structure without the need to implement the underlying functions of extraction, normalization, or joining from the disparate underlying data sources. Traditional data aggregation techniques may require data from one or more data sources to first be replicated and combined into a separate additional database(s) prior to conducting query(s). This requires agreements as to access, large amounts of storage for the replication/combining into separate database (s), and constant updating before meaningful analysis can be performed. The disclosed methods allow data to remain in silos and thus the data being accessed by a researcher or clinician includes the most up to date records and does not change the data structure of the data sources. In addition, the data integration schema allows users to select which data sources they wish to use as the basis for a given cohesive query without altering the structure of the query or resulting distributed data set representation to account for which specific data sources are included in the query. For example, including disparate sources of clinical data from different hospital systems would not change the structure of the resulting harmonized distributed data set from the user perspective if a new clinical data source is added to the query.

In some embodiments, the above-described systems and methods may be used to identify individuals who fall within certain categories of data type, or are similarly situated and used to identify, diagnose, treat, model, predict, and target various aspects of disease.

To the accomplishment of the foregoing and related ends, certain illustrative aspects of the system are described herein in connection with the following description and the attached drawings. The features, functions, and advantages that have been discussed can be achieved independently in various embodiments of the present disclosure or may be combined in yet other embodiments, further details of which can be seen with reference to the following description and drawings. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

FIG. 7 depicts example illustrations of data source-specific schema.

DETAILED DESCRIPTION

Figure 1:
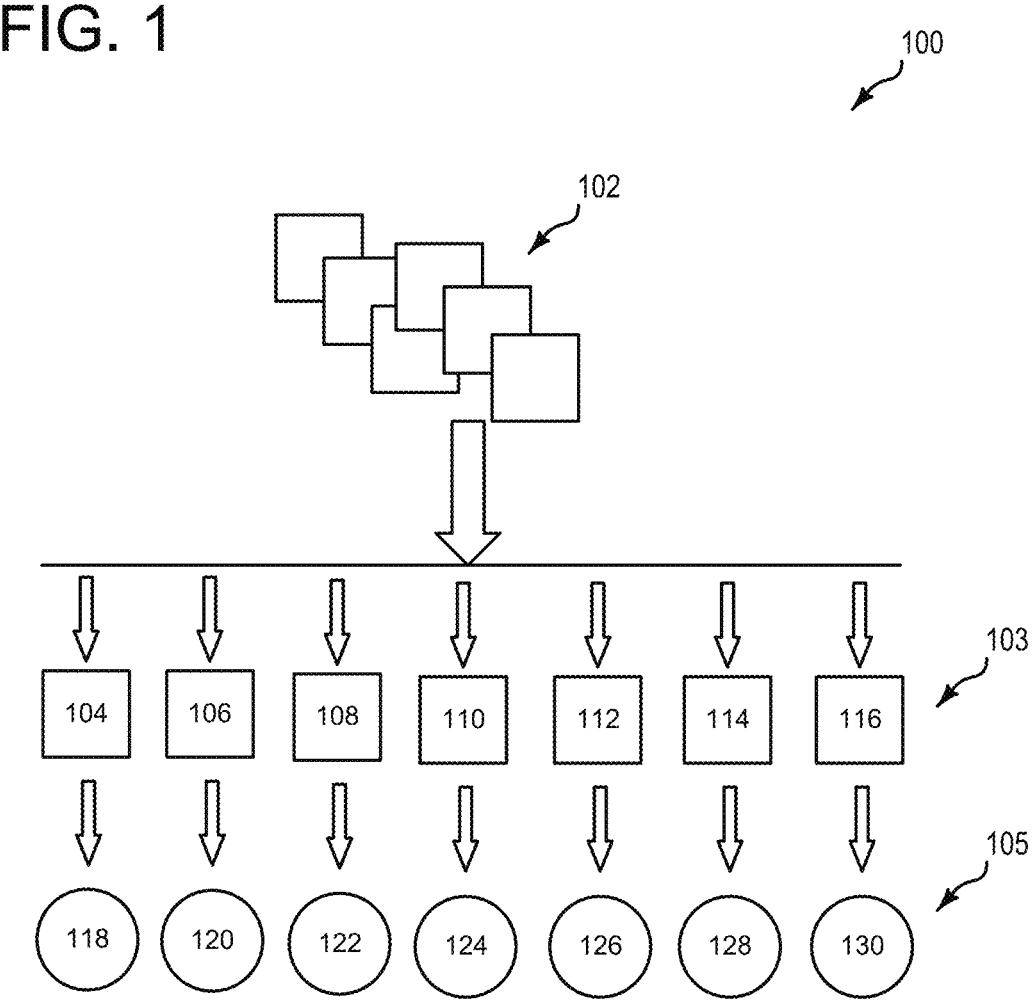
FIG. 1 is an example illustration of how biomedical data from patients are currently collected and stored.

"Hadoop Distributed File System" (HDFS) as used herein is a fault tolerant distributed file system designed to run on commodity hardware.

"Lustre" as used herein refers to a parallel distributed file system, generally used for large-scale cluster computing.

"NoSQL database" as used herein refers to high-performance, non-relational databases, that may utilize a variety of data models, including document, graph, key-value, and columnar. Examples of NoSQL databases include DynamoDB, Cassandra, Scylla, Accumulo, MongoDB, SequoiaDB, Riak, and the like.

"Network File System" (NFS) as used herein refers to a distributed file system protocol originally developed by Sun Microsystems in 1984.

"Data Source Object" as used herein means a distributed data set with a specialized schema that has been loaded from the data source.

"Resilient Distributed Data Set" (RDD) as used herein refers to an example of a distributed data object/set. In one context, the RDD refers to a fundamental data structure of Spark. The RDD comprises an immutable distributed collection of objects. Each dataset in RDD may be divided into logical partitions, which may be computed on different nodes of a cluster. RDDs may include any type of Python, Java, or Scala objects, including user-defined classes. An RDD is a read-only, partitioned collection of objects. RDDs may be created through deterministic operations on either data on stable storage, or other RDDs. RDDs comprise fault-tolerant collections of objects that can be operated on in parallel. They are a distributed memory abstraction that lets programmer perform in-memory computations on large clusters in a fault-tolerant manner.

"Apache Spark" as used herein refers to an open source parallel processing framework for running large-scale data analytics applications across clustered computers. Spark can handle both batch and real-time analytics and data processing workloads. Spark can process data from a variety of data repositories, including but not limited to the Hadoop Distributed File System (HDFS), NoSQL databases, and relational data stores.

"GraphX" as used herein refers to Apache Spark's API for graphs and graph-parallel computation.

"MLLib" as used herein refers to Apache Spark's scalable machine learning library.

"Data store" or "data source" as used herein refers to a repository for storing collections of data organized in a particular manner, such as a database, a file system, or a directory.

"Elastic MapReduce (EMR)" as used herein refers to a programming framework that supports the processing of large data sets in a distributed computing environment. EMR supports workloads including, but not limited to, Spark (see above).

The term "foreign key" as used herein refers to a parameter that serves as a restraint on data that can be entered on a database table.

Description

The following description relates to systems and methods for integrating a plurality of biomedical data for one or more individuals from a variety of data sources. Such data may be used for diagnostic purposes and/or to assemble subpopulations, or cohorts, with similar symptomology, genetic profiles, test results, and related criteria, including, but not limited to, age, gender, lifestyle, and risk factors. Information from such subpopulations may be used for a variety of purposes including, but not limited to, the identification of diagnostics and diagnostic criteria, effective and ineffective treatment protocols, potential drug or other treatment targets and the like. In some aspects, such information may be used to predict disease occurrence or treatment outcomes, diagnose, and treat individuals with similar profiles.

When undergoing diagnosis and treatment, patients generally meet with a practitioner, provide an oral history, receive a physical exam and receive one or more diagnostic procedures including, but not limited to blood draws, saliva testing, imaging, biopsies, and genetic profiling. Each type of biomedical data is generally stored or siloed in data sources on one or a plurality of computers over one or a plurality of public/private/hybrid networks, limiting access to data for a specific individual, as well as the identification of similarly situated individuals, thus preventing the use of the accumulated medical data available for a given disease, condition, or risk factor.

Currently, each type of biomedical data for an individual patient is typically stored in isolation in a data silo on one or more computers attached to one or more networks. A data silo is a data system that is incompatible or not integrated with other data systems. This incompatibility may be due to the file format, technical architecture, application architecture, or data architecture of the data systems. For example, biomedical records may be stored in a plurality of different formats such as, but not limited to, ASCII, JPEG, GIF, diagnostic imaging, FASTA, BED, 2 bit, GTF2, GFF3, PSL, BigBED, BedGraph, wiggle, BigWig, bowtie, SAM, PSL, BAM, HL7, X12, CCR, CCD, C32, CCDA, DICOM, TIFF, PNG, formatted text, plain text, PDF, database structures, ISO, compressed files, and XML. Further, each storage type or data source, may have specific protocols for accessing the data, requiring a user to understand the structure and search requirements of each data source. For example, clinical records may be stored in relational databases such as SQL or flat csv files; genomic data may be stored as flat VCF (variant call format) files or in a computational datastore such as GenomicsDB; annotations may be stored in databases, flat files, or third party web services; and images such as stained tissue samples, X-rays, and MRI images may be stored in an image format or processed data in flat files. Even within a specific data set, information may be stored in a distributed manner among one or more storage devices complicating access and analysis. On an individual basis, the relatively recent adoption of the electronic health records (EHR) system (also referred to as electronic medical record (EMR) system), which may include a basic health record of a patient, has presented numerous challenges to individual care. There are a wide variety of EHR platforms on the market and functionality varies within each system. Data entry can be inefficient and time-consuming. Such systems may additionally be proprietary and may not communicate easily with one another. Further issues can include slow processing speeds, formats that are not user-friendly, and/or limited capabilities. Even systems that are supposed to provide compatible data may be difficult to use, providing barriers to access of full medical records for an individual, let alone comparison of data among groups of similarly situated individuals. For example, data within a data set may be organized in any of a variety of ways (e.g., rows and columns, columnar, one or more hypercubes, etc.) with any of a variety of indexing mechanisms and labeling schemes. Coordinating access to data arranged using such different systems creates barriers to access of a complete set of health care related information for any particular patient or group of patients. Without knowledge of similarly situated individuals, a medical practitioner may order additional testing and design treatment plans that have been shown to be ineffective or less effective in similarly situated individuals, increasing health care costs and delaying effective treatment of an individual patient.

As mentioned above, computational operations on data stored in silos are currently done in a serial manner. Due to the serial nature, computational run time increases exponentially as the number of data sources and operations to create a desired cohort increase. As well as being stored in different formats, biomedical data may additionally be stored using different storage technologies. For example, in some aspects, the information may be stored locally or on a single device, it may be stored in a cloud computing system (e.g., "the cloud"), or partitioned through a distributed network. Each record or record type may be isolated in a data silo stored in a variety of different locations such as a local file system; distributed file system including, but not limited to, NFS, RDFS, or Lustre; on the cloud, for example through a service including, but not limited to, Amazon Web service (AWS), Azure, Google Cloud or other on-demand cloud computing platform providing subscribers a virtual cluster of computers available through the internet; or via a web service. Accordingly, in one aspect, the system described herein provides a scalable robust and rapid methodology for compilation, cross-comparison and analysis of data stored in separate silos on one or more devices and/or networks, thereby improving the way data is stored, retrieved and analyzed, increasing the efficiency of desired operations and allowing for the identification and formation of relevant datasets of individuals with similar individual and disease genotypic and phenotypic characteristics.

The ability to compile, cross-compare and analyze all (or a desired subset) of the data for an individual or among a group of individuals allows for the provision of a variety of useful treatment and research options. For example, such a system allows for "one-click" reporting for a patient or group of patients (e.g., for Tumor board reporting); data analysis through the application of various types of machine learning (e.g., neural network) on more than one type of data in parallel, which may enable creation of a model or models which may be applied for early detection or susceptibility of particular characteristics of a particular disease or disorder; and rapid development of evidence-based treatment protocols. In one example, the above-mentioned applications (e.g., generation of cohort(s), one-click reporting, machine-learning, etc.) enabled by utilizing the methodology for cross-comparison and analysis of the data in separate data sources on separate machines may operate via an application program interface (API). In this way, the systems and methods of the present disclosure represent improvements to computer technology as it relates to the mining of medical data stored in silos for novel biological insights, generation of cohorts, etc. More specifically, as discussed above, the ability to compile and cross-compare all medical data for an individual or among groups of individuals is not currently a viable option due to the serial nature whereby such actions are currently be performed. In other words, conducting any meaningful analysis of medically-relevant data on an individual or group of individuals is currently prevented by the architecture (e.g., silos) whereby current medically-relevant data are stored and exponential increases in computational run-time as the complexity of the desired data to be obtained increases. The systems and methods described herein represent a monumental step forward in terms of being able to cross-compare medical data from individuals or a group of individuals without prohibitive computational run-time and without the arduous nature of performing such operations in a serial manner. In one relevant example, the systems and methods described herein enable the automation of data mining for novel biological insights on medical data stored in silos improving the functioning of current systems by decreasing computational run times and removing barriers to access that currently exist.

Consider a machine learning approach to mine biomedical data comprising a plurality of different varieties (e.g. genomic, image, scan) of data from a plurality of individuals. Given the way that medically-relevant data for individuals are currently stored, there is no way to automate such a procedure. However, using the systems and methods described herein, a user may readily make use of machine learning to uncover novel biological insights from a plurality of individuals, where said plurality of individuals each have one or more variety(s) of medically-relevant data. Novel biological insights which may include an indication that a particular age group of patients, each sharing a particular gene mutation and similar risk factors, may respond well to a particular treatment option, whereas individuals with the same mutation and risk factors, but a different age group, may not respond well to the same type of treatment option. Such information may have been challenging to ascertain in the past using conventional methods, but such information may be readily deduced using the approach described herein.

Turning now to FIG. 1, an example illustration 100 depicting how different types of biomedical data 103 are currently accessed and stored is shown. Specifically, one or more patients 102 may have visited their respective medical practioner(s) (not shown), one or more times for any number of health-related reasons and the biomedical data 103 may be stored in various data sources or silos 105 which may be independently located in the same or different machines and/or on the same or different networks. For example, the symptoms and/or recorded observations 104 may be stored in a silo in an EHR database 118; the genomic sequence data 106 may be stored in folders in a file system (silo) 120 including or containing flat files; the imaging data 108 including but not limited to histology images (haemotoxylin and eosin), tissue imaging, blood smear imaging, may be stored in an images silo 122; the scan data 110 including, but not limited to, MRI scans, position emission tomography (PET) scans, and computed tomography (CT) scans may be stored in a picture archiving and communication system (PACS) database (silo) 124; the ultrasound data 112 may be stored in an ultrasound database (silo) 126; the blood/plasma data 114 may be stored in a metadata database (silo) 128 (for example, an object-relational database management system with an emphasis on extensibility and standards compliance); and the any other kind of biomedical data 116 may be stored in a customized database(s) or silo 130. The data sources and devices on which they are stored may be paired in a one-to-one relationship in which each database is on a single device or as a plurality in which multiple data sources including databases may be stored on one device, or some data sources may be stored individually and some data sources may be stored together as desired. For ease of understanding, data sources and devices may be referred to by number, though the numbering is not intended to indicate the required or available number of data sources in the system. In some embodiments, a data source may be spread across a plurality of devices, by itself, or in combination with other data sources or portions of data sources. The systems and methods described herein may access one, two, three, four, or as many data sources as needed according to the type and source of biomedical data desired for a particular query. For example, a first set of biomedical data may be stored on first device, a second set of biomedical data may be stored on a second device, a first and second set of biomedical data may be stored on a third device while a third set of biomedical data may be stored on a fourth device, and the like, according to the architecture of the biomedical data storage system. Similarly, one or more data sources may be stored in the cloud and thereby distributed across one or more devices. The data in the various silos may be stored in one or more file formats using one or more file storage structures, accessible using one or more computing languages or APIs, and are generally not accessible from any one location, preventing practitioners from assembling or even easily accessing a full profile of any given individual. Thus, obtaining relevant information requires serial access of each data source and each data source or silo that is accessed and analyzed exponentially increases computational run-time.

Figure 2:
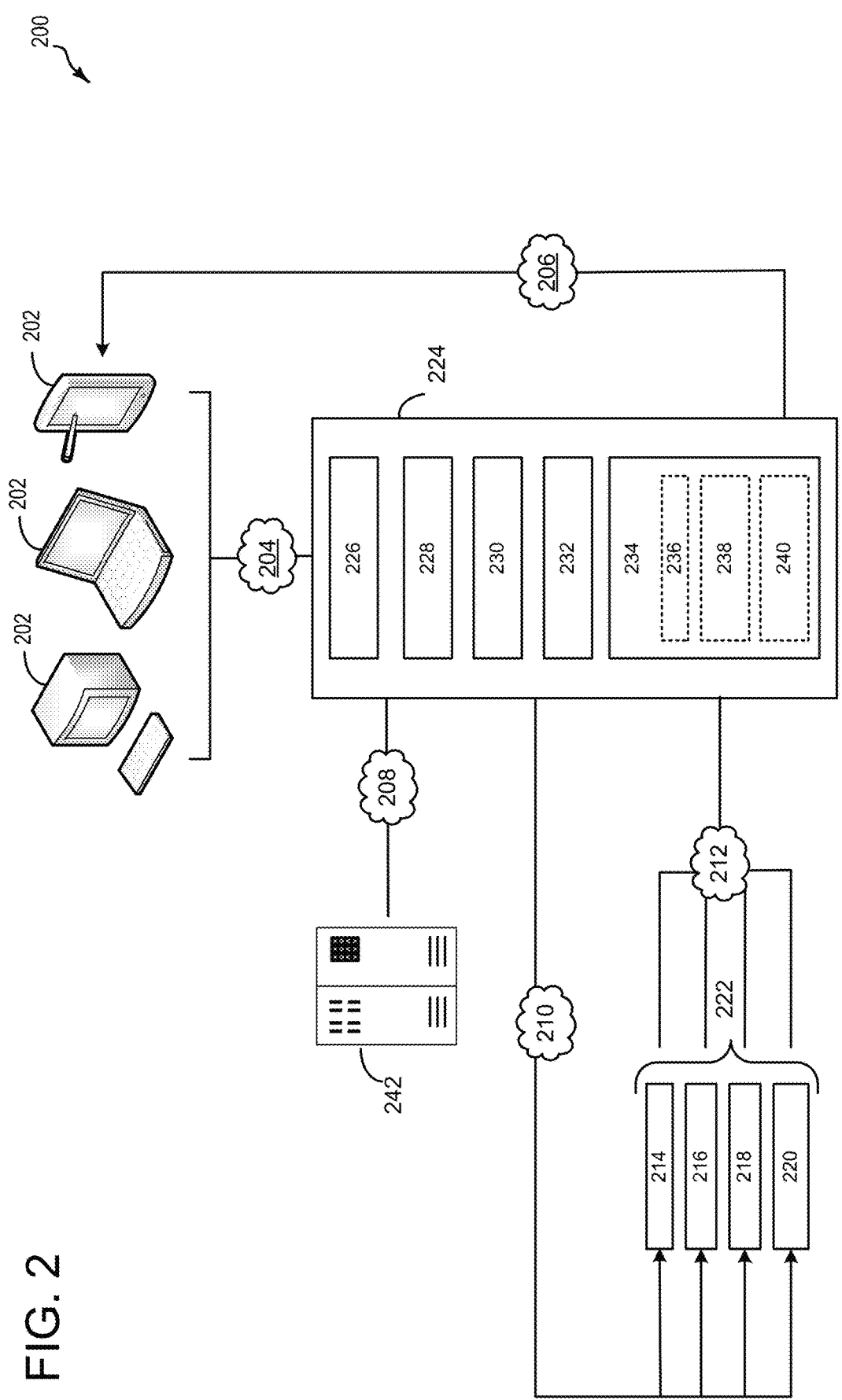
FIG. 2 is an example illustration of an overview of the system of the present disclosure.

Accordingly, turning to FIG. 2, an overview of a computer system 200 of the present disclosure is illustrated. Such a system may include one or more client devices 202 which interact through one or more networks 204, 206, 208, 210, and 212 with one or data sources 214, 216, 218, 220 (collectively data sources 222). Information may be transformed, processed, stored, or analyzed through one or more computing devices/servers such as integration server 224 or web server 242. In some aspects, such transformation, processing, storage, and analytics may occur in whole or in part on the client device. Client devices and/or other computing devices/servers may use one or more processors with one or more modules such as cohesive query module 226 or integration module 234; local data sources such as data source 228; and plugins such as add-in 232. Each module may include processor-executable instructions stored in memory to execute the methods described herein.

For example, a query is entered by a researcher, clinician, or other health professional via a client device 202. Client device 202 may be any computing or mobile device, for example, mobile devices, tablets, laptops, desktops, PDAs, and the like. The client device 202 may include a browser or other suitable application configured to access an integration server 224 via a data transmission network 204. Client devices that communicate with the data transmission network 204, may include, or be coupled to, display devices, storage devices, or other devices that may send and receive data to the integration server 224 and may remotely process or send data to be processed by the integration server 224 or another device 202. The devices 202 may interact with the computing environment over one of more network data transmission networks 204. Each communication within the system 200 may occur locally or over one or more public/private/hybrid networks 204, 206, 208, 210, 212 including, one or more of a wireless network, a wired network, or a combination of wired and wireless networks. Suitable networks include, but are not limited to, the Internet, a personal area network, a local area network (LAN), a wide area network (WAN) or a wireless local area network (WLAN). Information can further be received or transmitted over cellular networks either directly or through a base station. Additional servers 242 may be web servers, and/or may be part of distributed storage system representing one or more storage repositories configured for shared storage access for nodes within a cluster computing system using distributed computing technologies. Distributed computing technologies may create and/or store data sets that are not all attached to a common processing unit, but may be located in multiple computers in the same or different physical locations. They provide a means for partitioning data into batches of data that can be processed by a cluster computing environment in parallel by nodes of a cluster. Each distributed dataset may include or contain serialized data partitions that can be allocated to nodes in a distributed environment.

Network devices may include local area network devices such as routers, hubs, switches, or other computer networking devices. Storage devices may include, but are not limited to, secondary, tertiary or auxiliary storage, such as large hard drives, servers, and virtual memory. Storage devices may include portable or non-portable storage devices, optical storage devices, and various other media capable of storing, including, or containing data. In some aspects, web server 242 may perform various functions on behalf of integration server 224 in response to the user inputted query. For example, web server 242 may handle a portion of authenticating a user for a particular data source access or may handle a particular HTTPS protocol. As another example, web server 242 may handle sharing or publishing the results of the query generated by an instance of the integration module.

Figure 4:
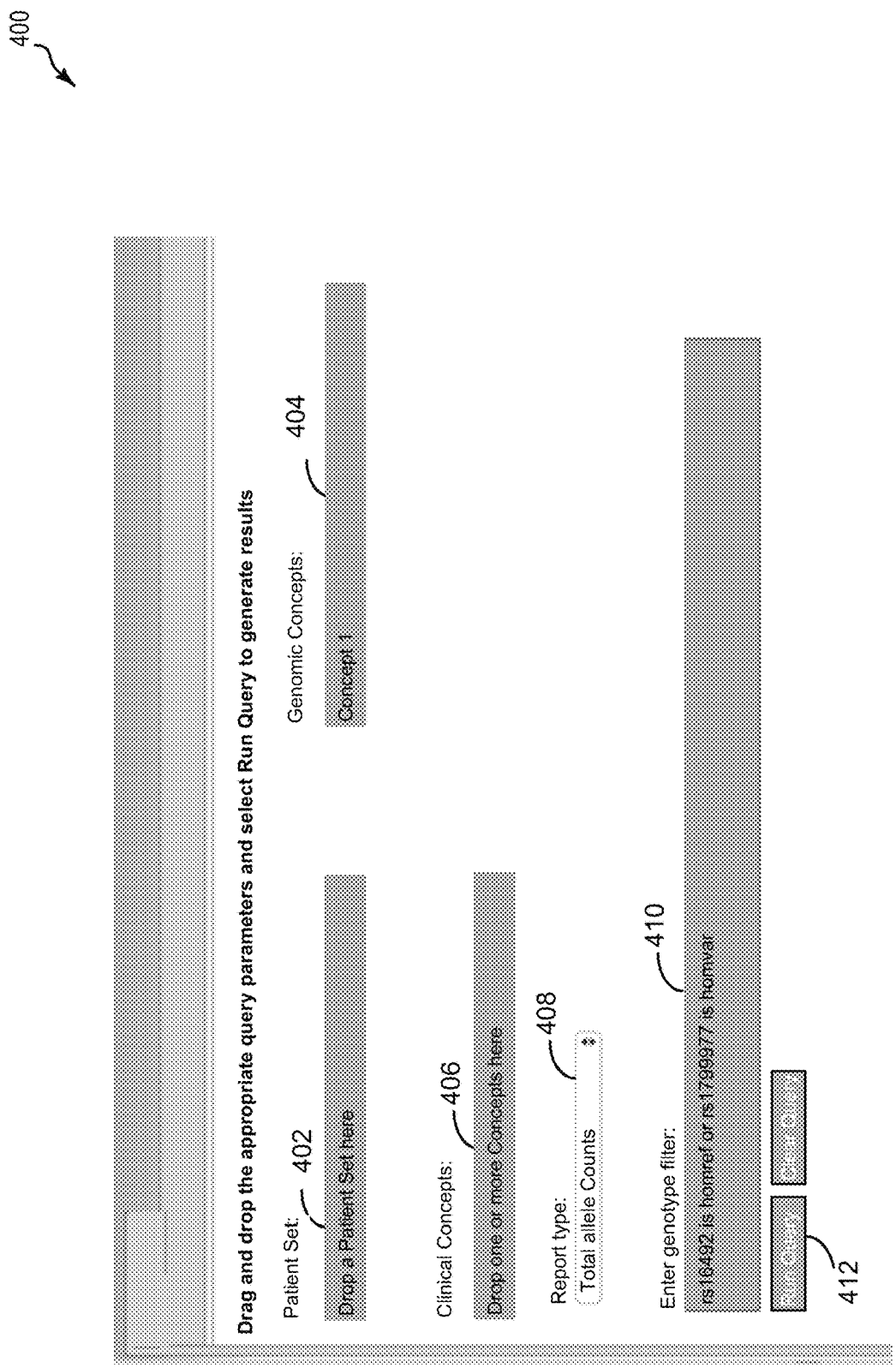
FIG. 4 depicts an example illustration of an interface for posing a particular query.

The query may be entered in any format generally used, including structured and unstructured formats. In some aspects, the query may be entered according to Boolean logic. In other aspects, the query may be created using a variety of drag-and-drop components or through the use of dynamic forms or prompts. In additional aspects, the user may be able to use the query environment to develop code to execute distributed queries. In further aspects, the query may be entered in plain English. An exemplary query using a pre-existing form is shown in FIG. 4.

The query, once inputted, is then converted to a cohesive query by a cohesive query module 226 and the type of information and the type of databases that need to be accessed in order to respond to the query is determined. The cohesive query generator may be located remotely, for example through a browser acting with integration server 224 or be locally installed on the client device.

Figure 6:
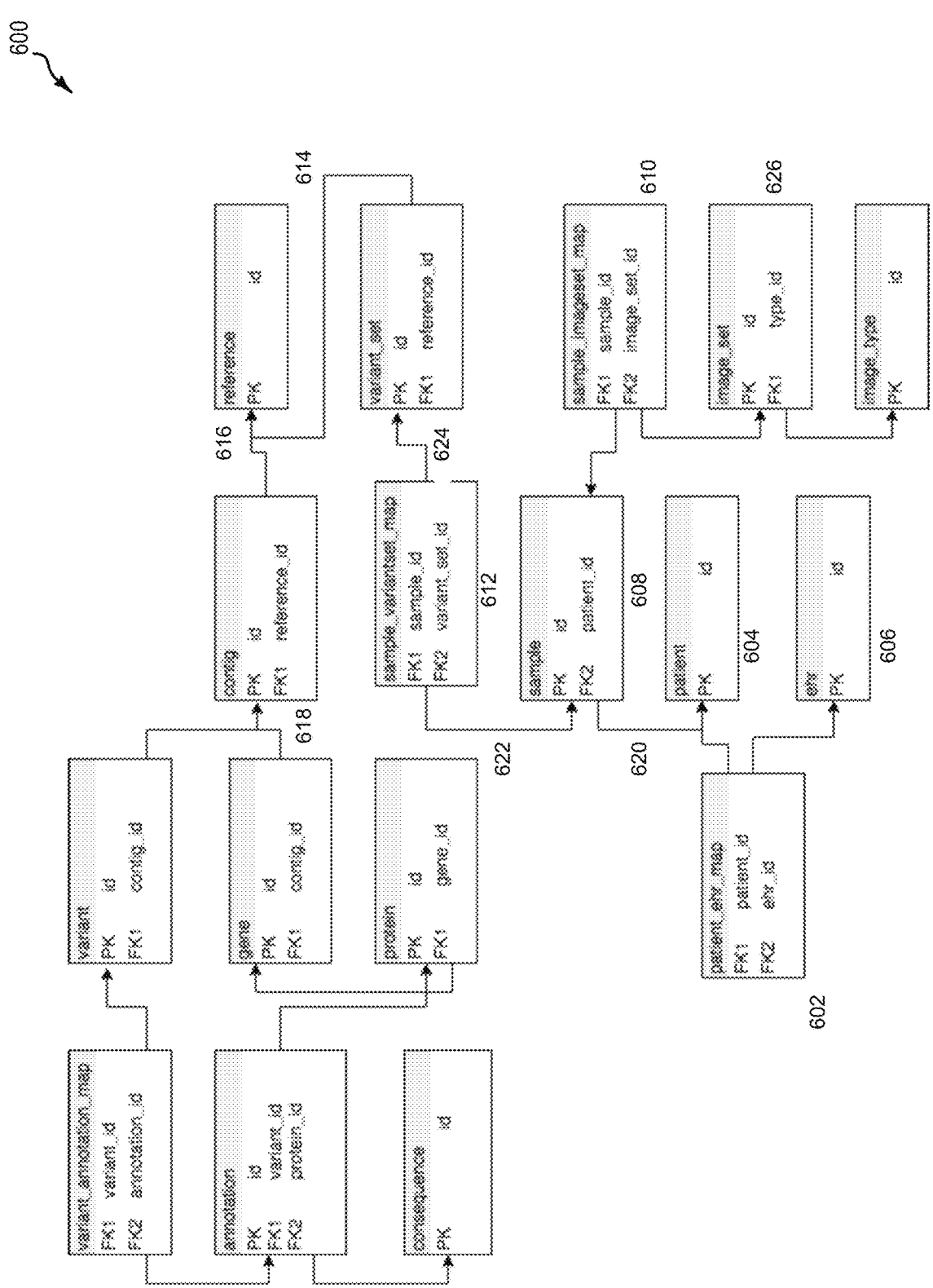
FIG. 6 depicts an example data integration schema of the system of the present disclosure.

The cohesive query module 226 filters the query through a data integration schema module or mapping database 230 populated by parsing configuration files for each potential data source which specifies relationships and overlaps between the sources through the use, for example, of foreign keys as shown in FIG. 6. The mapping database 230 does not store information from the source, but rather a reference to the source and the relevant associations within and among the sources (such as patient X in the EHR has a genomic sample Y that is stored in variant set Z). The data integration schema module may recognize the chain of dependencies among the sources and may access the desired information in the cohesive query without the user having to define each individual mapping. The mapping database may comprise, or may interact with a schema that defines the tables and constraints of the data integration schema, an import API to read data source metadata and populate the association tables, and an access API that is used during cohesive query execution to make relevant associations across the referenced data sources.

Aspects of the cohesive query (query segments) are then sent to an integration module 234, which may be part of the integration server 224 or may reside locally on the client device 202, and which may be associated with the relevant data source transformation and loading process. The integration module 234 comprises configurations for each of the data sources to enable communication with them. The integration module 234 is platform/language agnostic and compatible with distributed computing technologies. Each data source has a specific transformation and loading process that supports representation of the heterogeneous data in distributed datasets in structures specified by the schema in the data integration schema module 230. The data from each data source is extracted and filtered according to the structures specified by the data integration schema module 230 and records from data sources of particular types specifies how they are represented as a distributed object. This representation is based on common access/analysis patterns for the data type. For instance, genomic variant data queried from sources A and B (for example) with disparate internal representations of genomic variants will be returned to the user in the same standardized format defined in the schema of the data integration schema module 230.

Integration server 224 and client device 202 may implement the cohesive query and may communicate with one or more mapping data sources such as data integration schema module 230. Mapping data sources may include data and logic that may be implemented as modules in the memory of the integration server, client device, or both. For example, a mapping data source may include or contain a data integration schema which tracks associations and overlaps between disparate data sources in one or more data silos. The data source may be implemented by any conventional or other database or storage unit, may be local to or remote from integration server and client system, and may communicate via any appropriate communication medium. The integration server, the client device, or both may present a graphical user interface or other interface to solicit information from users and may provide reports including analysis results.

In some examples, the integration server 224 and/or cohesive query module 226 may include an add-in 232 or other suitable plug-in configured to confer additional functionality to integration server 224 or cohesive query module 226. However, in other examples, additional functionality may be built directly into the functionality of the integration server 224 or cohesive query module 226. For example, add-in 232 may provide the integration server 224 or cohesive query module 226 with specialized functions accessible by a user to perform additional tasks. For example, the add-in 232 or additional functionality may provide various functions which can directly interface with various specified data sources to import, format and update data provided by the integration server 224. For example, the add-in 232 or the additional functionality may provide various authentication options for accessing different data sources with different security requirements and may provide various filtering and display options for control of data presented to the user. Further, add-in 232 may preform aggregate queries in a distributed environment. The add-in 232 may query distributed data partitions, perform a specified analysis report within the distributed environment, and send the results back for visualization on the client device 202. The add-in 232 may provide a scalable and distributed way to operate on data partitions in parallel. For example, the master node of an EMR instance may serve as the entry point for queries that will be sent out to the secondary nodes and loading data from a particular data source. The partitions may be made available to the secondary nodes via a direct connection to the EMR file system, thus all partitions are available to each secondary node in the cluster. Add-in 232 may provide specific functions that utilize various parameters to manage data from specified data sources and to handle different data source and associated authentication procedures and data storage formats. For example, the add-in 232 may translate queries into a format that the data source will understand, (e.g., a format that is compatible with and/or able to be processed and/or parsed by the data source), for example through the use of the data integration schema module 230 which may be part of the add-in 232 or integration server 224. For example, in the case of genomics, a query for a gene name must be translated into genomic coordinates which are then mapped to the data source's positional and locational information. The data integration module may store metadata information about the data source instance and how the partitions map to genomic locations as defined by the reference genome of the original VCF files which may be utilized by the add-in 232 or the integration server 224 to create cohesive queries and query segments.

Data sources 214, 216, 218, 220 (collectively 222) and 228 accessible locally, or through networks 210 and 212, may be any suitable sources of data, for example, databases, web data servers, and proprietary data bases such as those associated with specific type of data including, but not limited to historic environment records (HER), EHR, GenomicsDB, PubMed, AWS EMR, CINAHL, Cochrane Library, EMBASE, TOXNET, LILACS, disease registries including, but not limited to the Global Alzheimer's Association Interactive Network, National Cardiovascular Data Registry, National Program of Cancer Registries, Clinical trials.gov, Drug Delivery Clinical Trials Database, Biological Specimen and Data Repository Information Coordinating Center, Biomedical Translational Research Information System, NIMH Clinical Trials, Yale Open Data Access, and the like. Any suitable data source may be accessed by integration server 224 once a path to the data source is specified. A path to a data source may be a network path including a URL, or a local path to a data source stored on the integration server 224 or client device 202. An administrator may register a data source by providing a path or address to the data source and security settings or other protocols. In some aspects, prior to or after the relevant data sources are identified, the user may be asked for authentication credentials to allow them to access the data sources including the information in which they are interested. Further, the integration server 224 and/or the data sources 222 may have security settings associated with it so that the user interface on the client device 202 may be configured to limit the view based on data components stored in the integration server 224 or through data stored outside in other data sources. The configuration for security may also utilize groups on account segment data to determine what data can be viewed by the specific user based on certain groups of data, such as locations, medical facility, or account.

Data relevant for the query is returned from the data sources via a network 212 to the integration sever 224 and integration module 234. The heterogenous data sets are joined through the integration layer module 236 based on the initial query and operations run on the data sets using operations module 238. For example, genetic variant data may be loaded from VCFs or from Genomics DB representations into distributed data objects based on a genomic-locus oriented organization of the data. The loading of genomic variant data into distributed data objects is supported by this locus oriented organization and is indexed by locus. The process of translating from VCF or Genomics DB representation is supported by a data source specific schema from each source, resulting in data source objects defined by the data source-specific schema that implement the data integration schema regardless of the data source. The methods and systems described herein allow for both joining data sets from disparate data sources representing the same type of data and more complex aggregate operations that integrate disparate data types as defined by the schemas of the data integration module 234 and identified by the user. This may thus allow users to select which data sources they wish to use based on the query without altering the structure of the query or the resulting distributed data set representation to account for which specific data sources are included in the query.

In some examples, computing environment 200 may include one or more clones (not shown) of integration server 224 that may be used in a distributed manner. Integration server 224 may additionally include a cache 240 for storing query results. For example, integration server 224 may process a query and store the results in cache 240 so that if integration server 224 receives the same query again, the cached result may be returned without any further processing. In some aspects, a query may be independently run each time it is entered. In other aspects, cached results may be used if a repeat query is entered within a specific time frame such as a set number of hours, days, weeks, or months. In such examples, the cache may temporarily store results according to an associated time constraint (e.g., an amount of time based on the specific time frame, such as an amount of time that is equal to or greater than the set number of hours, days, weeks, or months).

Figure 3:
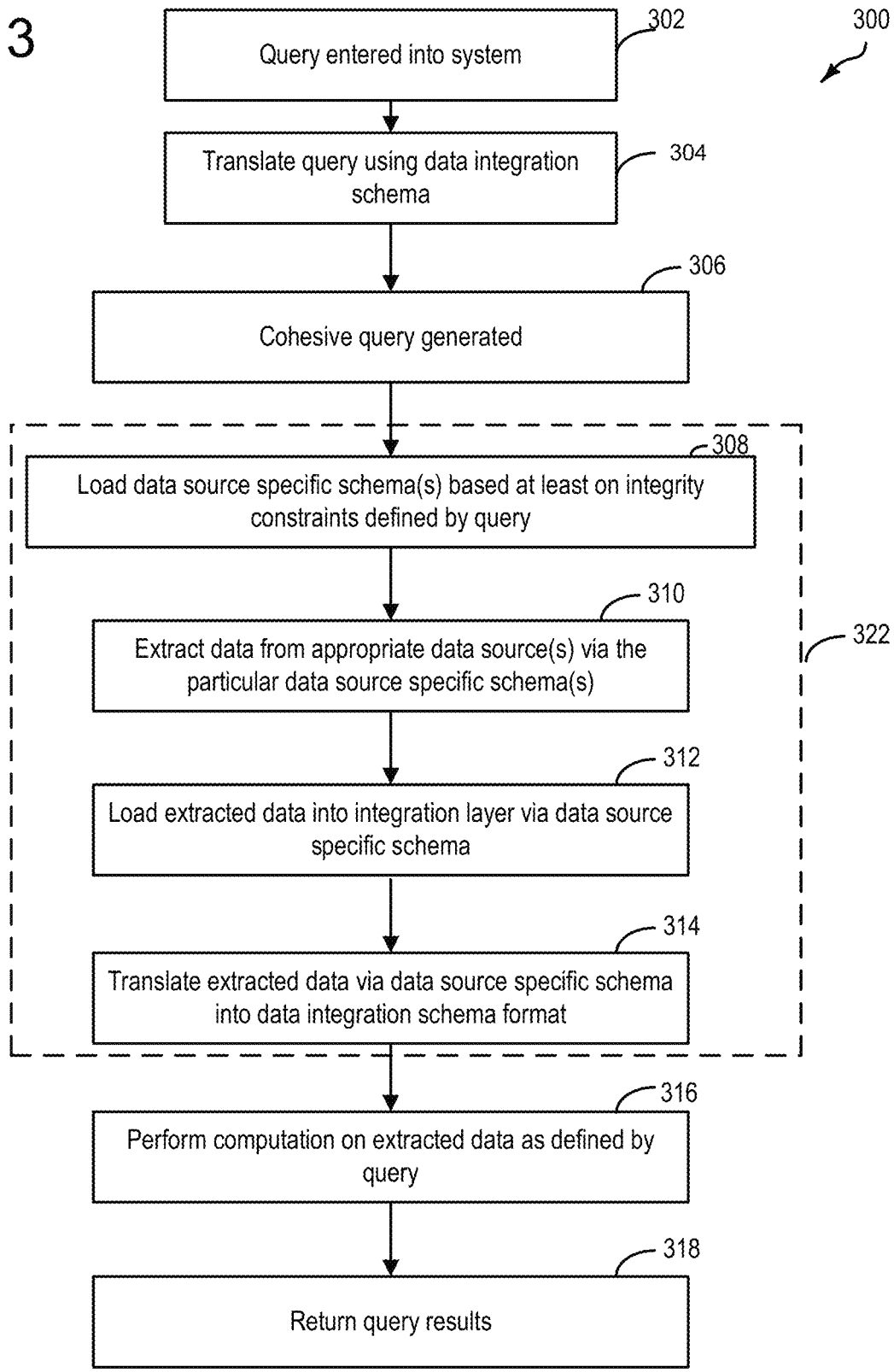
FIG. 3 depicts an example method for how a particular query is posed and results returned to a user.

Turning to FIG. 3, a high level method 300 is shown, for generating user-defined sets of information utilizing the systems and methods described herein. It may be understood that the methodology described with regard to FIG. 3 may be utilized where data sources for particular biomedical data have been created. In other words, FIG. 3 does not depict how or where data sources are generated/maintained, but rather depicts how such data sources may be utilized according to the methodology herein, to create subsets of biomedical data, whether such data is for a single patient, a group of patients, or for the formation of a cohort of patients. Additional aspects and details of the method of FIG. 3 are shown in FIGS. 8A-8B, 10, 11A-11B, 12, and 13.

As shown in FIG. 3, a query is entered into the system at 302. The query may be entered via a local application or through a web browser in any format generally used, including structured and unstructured formats. In some aspects, the query may be entered according to Boolean logic. For example, the query may include one or more of a disease, diagnosis, symptomology, genomic data, image results, and/or other biomedical data that may be included in a biomedical record. In other words, the query may be defined by a number of integrity constraints to structure the cohesive query. The query is then sent to a relational database and analyzed according to the data integration schema 304 and a cohesive query is generated at 306 according to the data integration schema 304. The cohesive query is used to identify the type of information and data sources useful in answering the query.

Data sources may have the same or different data structures. Data sources may be any suitable sources of data, for example, databases, web data servers, and proprietary data bases such as those associated with specific type of medical data including, but not limited to EHR, GenomicsDB, PubMed, AWS EMR, CINAHL, Cochrane Library, EMBASE, TOXNET, LILACS; disease registries including, but not limited to the Global Alzheimer's Association Interactive Network, National Cardiovascular Data Registry, National Program of Cancer Registries, Clinical trials.gov, Drug Delivery Clinical Trials Database, Biological Specimen and Data Repository Information Coordinating Center, Biomedical Translational Research Information System, NIMH Clinical Trials, Yale Open Data Access and the like.

Once a cohesive query is generated, including determining the type of information and data sources for the query, the query is processed via the steps depicted generally as block 322. While not explicitly shown, it may be understood that after the query is assigned to be processed, a master (also referred to as "primary" or "client"), may delegate to slaves (also referred to as "secondary" or "servers") via a cryptographic network protocol (e.g., SSH). The type of information and data sources for the query are mapped to data source specific schema as defined by the cohesive query for the relevant data sources at 308. For example, in the case of a genome, a query for a genome will be translated into genomic coordinates which are then mapped to positional and location information using a data source specific schema with metadata information about Genomics DB instances and how the partitions map to genomic locations as defined by the reference genome for the original VCF files. As another example, in the context of the EHR, a query may request treatment events associated with a specific treatment modality (e.g. particular drug, particular administration route, dosing, etc.), for a set of patient identifiers. In such an example, the data integration schema may map such requests from their conceptual representation in the data integration schema into queries to the relevant data sources, which may then be retrieved from the data sources and reverse translated to the data integration schema representation of the relevant concepts. In another example, if the query included a request for particular scan data, then the data source specific schema (defined in the context of the data integration schema) may include data source specific schema information related to the scan data source (e.g., PACS DB). In still another example, if the query included a request for particular image data, then the data source specific schema (defined in the context of the data integration schema) may include information related to the image data source (e.g., Omero). In some examples, a query may include a request for more than one other type of biomedical data, such as image data and scan data, for example, at which point data source specific schema related to both databases may be retrieved.

The data source is then accessed at 310 and queried using the language appropriate for the specific data source based on the mapped integrity constraints of the data source specific schema in the context of the cohesive query. As one example, a user may enter a query related to variant information and thus a request may be sent to a genomics database. Additionally or alternatively, the user query may include a request for image data and thus the image data source may be queried for particular images. In some aspects, a security protocol may be required or initiated before granting access to the information in the data source.

The information is then extracted from the data source at 312. In some aspects, the information is extracted and stored in a database. The stored information may be updated manually or automatically as additional records of interest are added to the data source at 312. The extracted data is returned, for example, to the integration module or data integration schema module of FIG. 2, which maps the data in reverse, integrating data from different sources by reassigning the field or fields used by the data source to those of the modules and combining the resulting information from disparate data sources and data types into a cohesive whole at 314 attached to a distributed data sets. Steps included at 322 may be performed serially, in parallel, or in a distributed manner on one or more data sources. The resulting collection of data is then analyzed as a set at 316. For example, the collection of data may be submitted as a Spark job with the data and requested analysis.

Requested analysis may include generation of a cohort with particular attributes such as age and genomic variants, or age and similar PET scan results, etc. Other examples may include particular symptomology, demographics, and genetic variants, particular symptomology and particular image data (e.g., tissue samples), etc. Virtually any type of analysis may be implemented at 316 which comprises some sort of combination of EHR data and other biomedical data. In some examples, the analysis at 316 may include machine learning of some kind. For example, machine learning may be used on particular data set(s) in order to reveal novel biological insights, for example. Such insights may include associations not obvious to a user, such as a particular lifestyle choice and genetic variant as they relate to a particular disease, for example.

The results of the analysis are then presented at 318. In some examples, the results may be written to a relational or non-relational database, as an aggregated set. It may be understood that the data written at 318 is dependent on the analysis procedure. After finishing the analysis and/or writing the results of the analysis to the data source, a success return code may be sent, for example to an add-in as shown in FIG. 2 signaling the add-in to read the finished analysis from the data source and the results may be sent to the application on the client device. In this way, a user defined query may return the desired result, without prohibitive computational run-times.

Turning to FIG. 4, an example of a query interface 400 for a genomic analysis is shown. The query interface 400 may be displayed as an interactive graphical user interface on a display integrated in or in communication with a device on which the query is input, such as client device 202 of FIG. 2. Input to the query interface 400 may be provided via one or more input devices, such as a peripheral or integrated mouse, keyboard, touch screen, microphone, camera, and/or other input mechanism associated with the device on which the query is input (e.g., the client device). The user selects a patient population set at 402. The population set may comprise a subset of samples of a particular dataset, where the subset may be based on the criteria deemed to be relevant to the query. For example, the population set can include, but is not limited to any clinical or genomic concepts such as particular genomic reads mapped to particular clinical entity (s), one or more biopsies, ICD10 codes, particular demographic information, image data, etc. In some examples, the population set may comprise a random set for cross validation studies, statistical analysis, etc. Genomic concepts including, but not limited to, a specific genomic location may be entered at 404. Clinical concepts such as ontology, ICD10 codes, and the like may be entered at 406 and the report type may be selected at 408. In some aspects, additional fields may be provided, allowing the user to search for clinical attribute distributions for a specific position in the genome, limiting the query to a specific genomic location, or a specific attribute within the specified concept as shown in 410. The query may then be run by selecting "run query" at 412.

Figure 5:
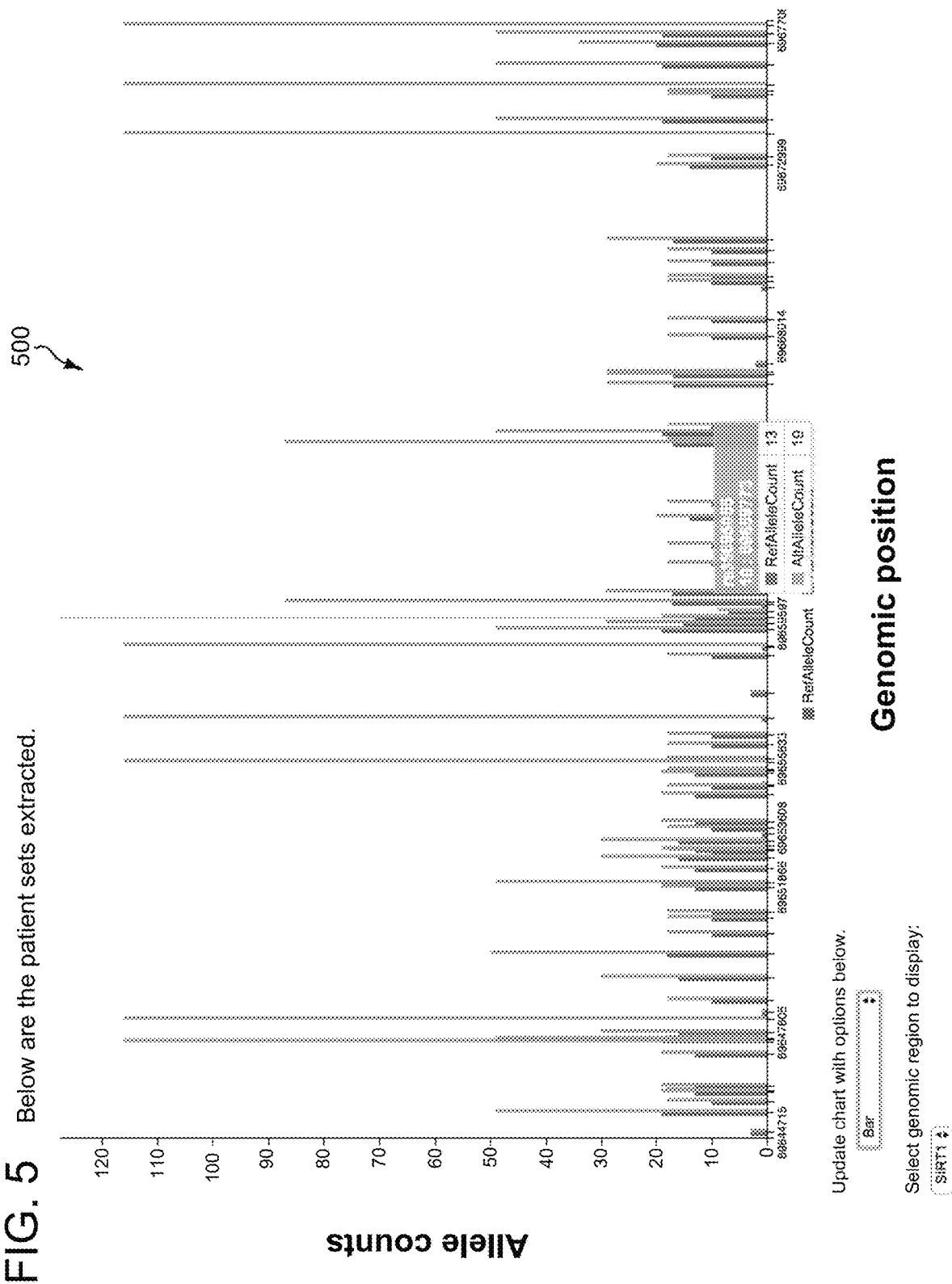
FIG. 5 depicts an example illustration of results which may be returned to a user after posing the particular query depicted at FIG. 4.

In FIG. 5, exemplary results 500 from the query of FIG. 4 are shown in a total allele report plotting allele counts vs. genomic position. In some examples, results such as the illustrated results 500 may be displayed on a display device, such as a display of client device 202 of FIG. 2. In results 500, the total allele report counts provides the reference and alternate allele counts at each variant location within the selected genomic region for the patients provided. Reference allele count is computed as the sum of the heterozygous counts and double the homozygous reference counts. Alternate allele count is computed as the sum of the heterozygous counts and double the homozygous alternate counts.

A single data source, such as the genomics databases accessed in FIGS. 4 and 5, may contain or include some, but not all, of the data needed to respond to a query. As each data source may contain or include one or more file formats using one or more types of data architecture or dictionaries, a data integration schema as shown at 600 may be used to integrate data from disparate sources in different formats into a cohesive whole that may be analyzed. As shown in FIG. 6, the relationships between data in various silos and/or data sources may be stored in a data integration scheme implemented as a relational database that holds association tables between the various data sources and the integrity constraints (foreign key dependencies). For example, a first association table may be related to an at least one further association table via a primary key-foreign key relationship. Such a relational database may be stored, for example, within data integration schema module 230 shown in FIG. 2. The data integration schema includes parsed configuration files for each of the data sources specifying relationships and overlaps between the fields across data sources.

FIG. 6 depicts a schema specific for genomic information. As shown at 602, data from an EHR may be mapped as two foreign keys (FK) including patient identification information and record information. The foreign keys are mapped to primary keys (PK) for patient ID at 604 and EHR ID at 606. The information in the EHR 602 relates to a sample data source 608 which may be located together or separately from the EHR. The sample 608 has an ID and a patient ID which may be the same or different as the code used for the patient ID in the EHR record. The sample 608 may be associated with an image 610 which may be stored in the same or different data sources as the patient EHR record. The sample 608 is additionally associated with a variant set map 612 which includes or contains a sample id and a variant_set_id.

The integrity constraints represented by the foreign keys (FK) in FIG. 6 may be any constraints associated with the specific database and information being accessed. Constraints may be based on any field or set of fields existing in the data source. For example, a sample could be constrained by the origin, that is, blood, tissue, or bone; the location from which the sample was obtained; the collection date; the cell type; or the cell line. The variant set could be constrained by testing methodology, that is RNA-seq, microarray, mass spec genotyping, CT, MM, Pathology/Microscopy and/or the genotyping instrument (e.g., Illumina HiSeq, Illumina MiSeq, PacBio sequencer, and the like). The call quality could depend on the variant. The variant could specify the variant type, e.g., SNP, indel, transversion. An annotation could include or contain the genomic region such as intergenic, coding, noncoding, regulatory region. The image set_map 610 could specify the imaging instrument. The image set 626 could specify the image format.

For example, the integrity constraints for an EMR cluster may include patient information such as demographics; medication; medical history; laboratory results; diagnoses; physical signs; imaging results; and/or date of visit. Laboratory testing data sources may include constraints regarding patient information, demographics, types of tests, conditions under which tests were taken (e.g., fasting/non-fasting, time of day), test results, and the like. As shown in the exemplary genomic schema in FIG. 6, a variant set may be dependent on a single reference genome (614), a contig may be dependent on a single reference genome (616), a gene may be dependent on a single contig (618), a sample may be associated to a patient (620), and a sample may be represented in a variant set (622), and multiple samples can exist in a variant set (624). Similar relationships may be mapped between disparate data sources for other types of information useful for other types of queries.

The data integration schema as shown in FIG. 6 may be used to generate a cohesive query, and identify the data sources and information needed from the data sources to address the question posed in the query. Aspects of the query relevant to a particular data source may be parsed out (e.g., defining query segments). Each data source may be in the same or different formats using the same or different file types and structure. Thus, as shown in FIG. 7, data source specific schema may be utilized to translate between the data source and the data integration schema to select and extract the data requested to respond to the query.

FIG. 7 shows an exemplary data source-specific schema for a data source including or containing VCF (variant call format) files. VCF files are particularly problematic to search and analyze as genomic data, and while inherently more structured than EHR data, poses a data storage problem. Instead of explicitly storing the nucleotide sequence of all $6 \times 10^9$ base pairs for each genome, data are commonly compressed into VCF files that itemize locations where a particular individual's genomic sequence deviates from a reference genome. Considering that the difference in genomic sequence between humans is approximately 0.1%, by storing the variants, VCF files achieve a significant degree of lossless compression and can be unambiguously indexed by chromosome and nucleotide position. However, difficulty arises when trying to aggregate VCF files into a comprehensive data store due to sparsity. Relational databases in general do not readily accommodate efficient handling of sparse data that are inherent to the VCF specification. Genomic variant data can be conceptualized as a two-dimensional matrix, with genomic positions on the horizontal axis and samples on the vertical access. Under this representation, cells of the matrix store data about the sample for the given position—this data could include multiple fields such as alternate alleles, genotype, read depth, and quality scores. Since the majority of the genome is identical to the reference, the columns of this matrix is expected to be sparse. Further, genomics databases such as GenomicsDB are frequently heavily distributed. Partitions could be defined by splitting a matrix, such as the one described above, into vertically or horizontally sliced regions, can be organized across multiple machines, and must be jointly queried in order to obtain the relevant information. Previously, accessing information in such a database required a user to manually organize the variant data partitions across the various nodes, preventing the use of distributed file systems and requiring secondary nodes. The use of a data integration schema such as the example shown in FIG. 6 maintains specific mappings for VCF files in a genomic data source, biological entities (reference genome, contig, genes, proteins, variants, annotations), samples, patients, electronic health record system, and imaging data sets. The data integration schema does not store information from the source, but a reference to the source and the relevant associations within and among the sources such as patient X in the EHR has a genomic sample Y that is stored in variant set Z. The use of the data integration schema in FIG. 6 with the data source specific schema such as the example shown in FIG. 7 allows for the querying of heterogeneous data stored in disparate data sources without requiring manual organization of data partitions across various nodes and allowing the use of distributed file systems for research and analysis.

Figure 8A:
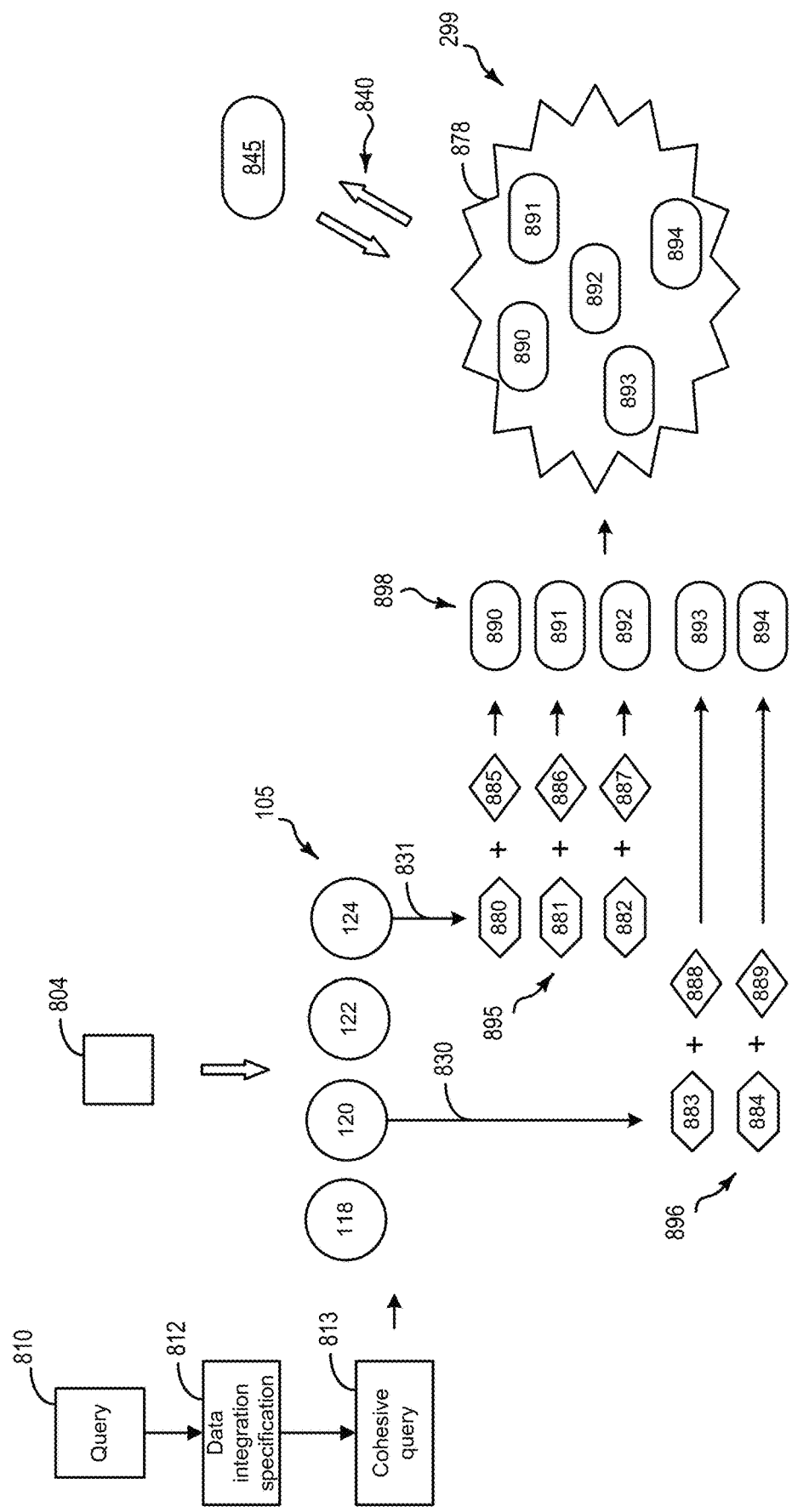
FIG. 8A depicts an example schematic illustration of how particular data source objects are generated for a particular individual.
Figure 8B:
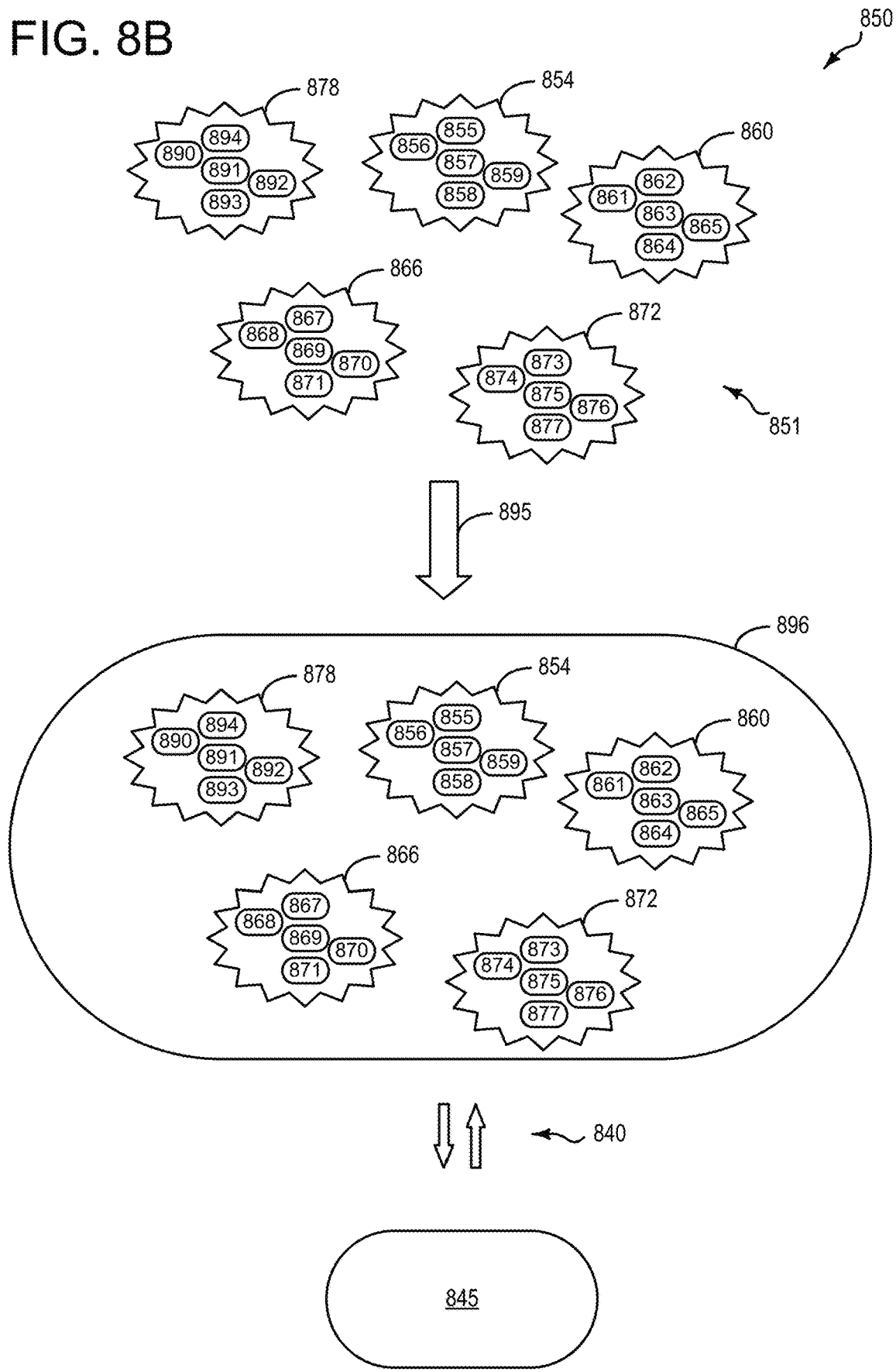
FIG. 8B depicts an example schematic illustration of how one or more data source objects may be combined into a data pool.

Turning now to FIGS. 8A-8B, they depict example schematic illustrations whereby biomedical data may be accessed and transformed into data source objects that may be included in a data pool and analyzed according to the methods of FIG. 3. Turning to FIG. 8A, various biomedically related data, (e.g., 103) not shown in this example, may be acquired from one or more individuals 804, and may be stored in various silos 105. As an example, genomics file system 120 may include various types of data, including but not limited to whole genome sequences, variants, transcriptomics data, etc. As another example, scan database 124 may include but is not limited to MRI data, PET data, CT data, etc. Other databases 118 and 122 may include other types of data, as discussed above. For illustrative purposes, illustration 800 focuses on a query specific for data included in genomics file system 120 and scan database 124.

In the context of this disclosure, query 810 is input via a user into a client device. The query is then translated via the comprehensive data integration specification 812, as defined by the data integration schema, into cohesive query 813. As discussed above, the comprehensive data integration specification 812 includes configurations for each of the data sources (each of silos 105) including integrity constraints, to enable communication with each of the data sources as specified by the query. The comprehensive data integration specification 812 allows for instructions to integrate data as specified by the query into the data integration schema, and to maintain data source-specific mappings that can map the relevant data to the data integration schema.

In the simplified schematic depicted at FIG. 8A, data 895 and data 896 are extracted from the desired silos 120 and 124, respectively, via a first data source-specific schema 830 and a second data source-specific schema 831. As discussed above, the (first and second) data source-specific schema may be generated as a function of the integrity constraints and data integration schema. In this particular example, data 896 corresponds to whole genome sequence data 883, and variant data 884, while data 895 corresponds to MRI data 880, PET data 881, and CT data 882. The disparate internal representation of data particular to the data source type and the data source format will be returned in the same standardized format defined in the data integration schema based on common analysis of the data type as well as the operations used to support aggregate queries.

The genome sequence data 883, variant data 884, MRI data 880, PET data 881, and CT data 882 are then attached to distributed data objects 888, 889, 885, 886, and 887, respectively, to generate data source objects 898. Specifically, data source object 893 comprises a distributed data set with data acquired through data source-specific schema 830, loaded from data source 120, and represented in accordance with the data integration schema. Data source object 894 comprises a distributed data set with data acquired through data source-specific schema 830, loaded from data source 120, and represented in accordance with the data integration schema. Data source object 890 comprises a distributed data set with data acquired through data source specific schema 831, loaded from data source 124 and represented in accordance with the data integration schema. Similarly, data source objects 891 and 892 comprise distributed data sets with data acquired using data source specific schema 831, loaded from data source 124 represented in accordance with the data integration schema. It may be understood that data source objects 890, 891, 892, 893 and 894 comprise data source objects in data integration schema format.

Data source objects 890, 891, 892, 893 and 894 are then combined or joined into data pool 878 based on the integrity constraints and the comprehensive data integration schema. In this way data source objects may be joined as a function of desired analytics as defined by the user. Such a mechanism allows for support in joining data sets from disparate data sources representing the same type of data (e.g. whole genome sequence data 883 and variant data 884), or more complex aggregate options such as that depicted at FIG. 8A as defined by the data integration schema and identified by the user. In some examples, data pool 878 may comprise a distributed data set for which each of the data source objects 890, 891, 892, 893 and 894 are attached. Said another way, data pool 878 comprises one or more distributed data sets. Once in the data pool 878, computations 845 may be conducted via APIs 840. APIs 840 are defined in reference to the data integration schema representation of data source objects such that the user-defined query may expect consistent or expected values for a particular query concept, regardless of the initial data source from which the data was extracted.

For example, genetic variant data may be loaded from VCFs or from Genomics DB representations into distributed data objects based on a genomic-locus oriented organization of the data. The loading of genomic variant data into distributed data objects is supported by this locus oriented organization and is indexed by locus. The process of translating from VCF or Genomics DB representation is supported by the data source specific schema from each source, resulting in distributed data sets that implement the data integration schema regardless of the data source and allowing for joining data sets from disparate data sources.

While FIG. 8A depicts an example where data for a particular patient or a specific set of data for a group of patients may be extracted and joined, there may be other examples where it may be desirable to conduct analytics on across sets of data. Turning to FIG. 8B, an example illustration 850 is depicted, illustrating how a plurality of data pools 851 comprising data pool 878, data pool 854, 860, 866, 872 are combined into data pool 896. For illustration 850, it may be understood that data pool 878 corresponds to multidimensional data from a first patient, data pool 854 corresponds to multidimensional data from a second patient, data pool 860 corresponds to multidimensional data from a third patient, data pool 866 corresponds to multidimensional data from a fourth patient, and data pool 872 corresponds to multidimensional data from a fifth patient. For each data pool corresponding to each patient, there are five data source objects. As depicted at FIG. 8A, data pool 872 includes data source objects 890-894 corresponding to data extracted from data silos 120 and 124. Thus, while not explicitly illustrated, it may be understood that each of data pools 854, 860, 866, and 872 include corresponding data source objects of similar nature to those of data pool 878.

Data pools 851 may be combined or joined 895 into data pool 896. Once in the data pool 896, computations 845 may be conducted via APIs 840, as discussed above. In this way, a query may return results to a user that includes data across any number of patients and any number of biomedical data types.

With regard to FIGS. 8A-8B computations/analytics 845 may include machine learning, which may include deep learning. Machine learning methods may include but are not limited to linear regression, logistic regression, elastic nets, singular value decomposition, restricted Boltzmann machines, Markov chains, latent dirichlet allocation, association rules, gradient boosted decision trees, random forests, clustering techniques, and/or matrix factorization. Machine learning may be utilized to uncover medically-relevant insights via learning from relationships and trends in the data included in data pool 878 (FIG. 8A), or data pool 896 (FIG. 8B). As one example, machine learning may be utilized to generate cohorts of patients that fall in a certain category of data type, or certain categories of data types using the data in the data pools and/or other relevant information as input. In another example, applications 840 may include an application that may enable one-click reporting for a patient or group of patients. For example, a tumor board may comprise a group of doctors and/or other health care providers with different specialties which meets regularly to discuss cancer cases and share knowledge, with the goal of determining most appropriate possible cancer treatment and care plans for a particular patient or group of patients. In such an example, machine learning may be used to recognize trends in the data stored in the data pool (e.g. 878 or 896), which may be useful to the tumor board. Specific examples may include trends comprising specific genetic mutations or groups of genetic mutations, and corresponding symptoms. In some examples, trends may include information as to what types of treatments are indicated as being at least partially effective in treating a patient or group of patients with a particular regimen, where the particular regimen may include a drug or set of drugs, diet, environment, radiation therapy, immunotherapy, or any other type of therapy regimen for treating a patient or patients with one or more tumors.

Such analytics may in some examples enable the generation of a unique model which may be used for identification of risk profiles or early detection disease in a particular patient or group of patients. As one example, consider a patient who presents a particular characteristic or characteristics, including but not limited to, a particular genetic mutation, and a particular lifestyle habit such as a history of smoking. In such an example, the characteristic(s) of that particular patient may be analyzed using application 840, where the application includes a model or models generated via machine learning conducted on the data core pool (e.g. 878). Comparison of the individual patient to similarly situated patients (see for example data pool 896) may predict a likelihood of that particular patient to developing esophageal cancer, for example. That patient may then be more closely monitored for the development of such a disease and effective treatments may be identified from the same or a similar analysis if the patient develops such a condition. Such an example is meant to be illustrative.

Figure 9:
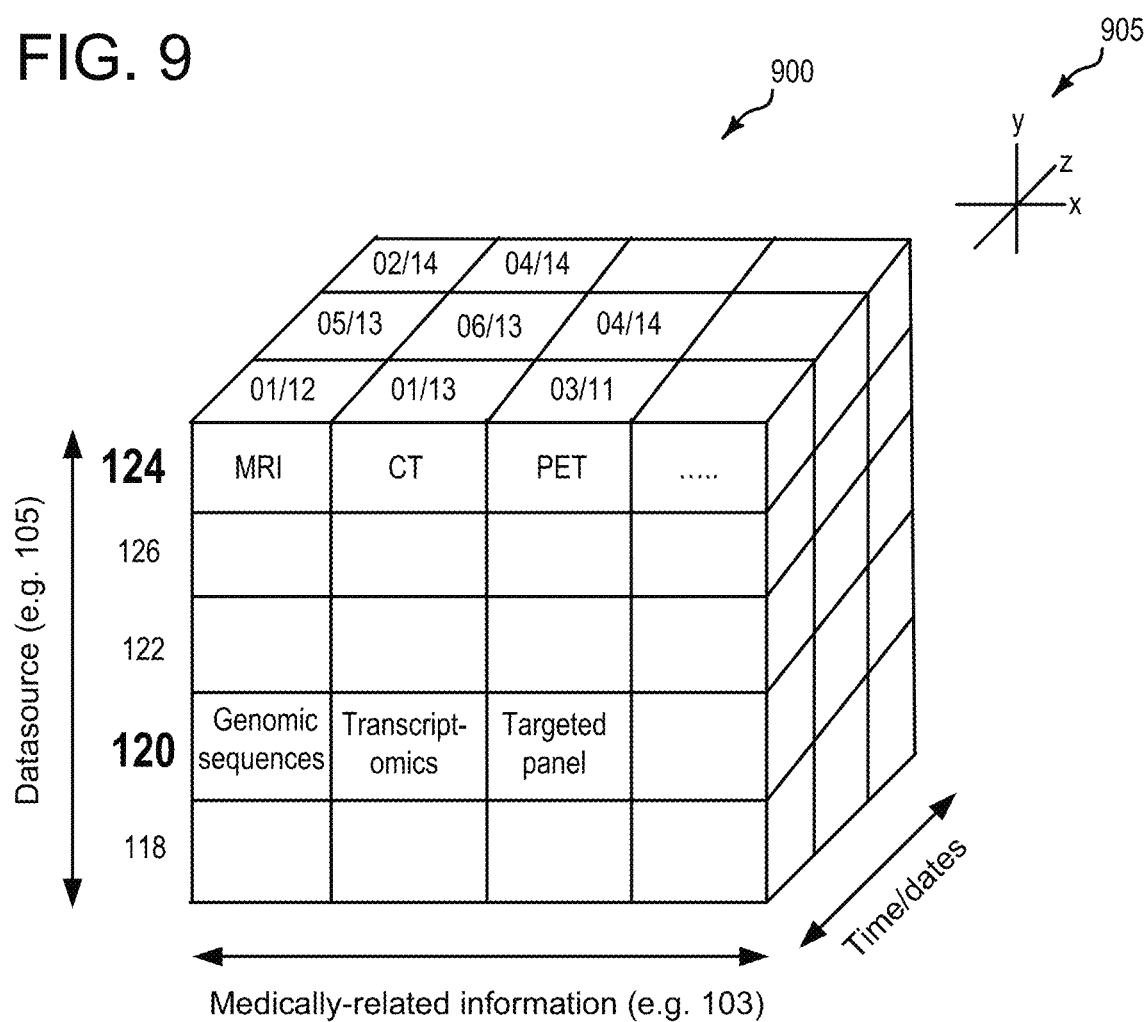
FIG. 9 depicts an example of a multidimensional data object.

While FIGS. 8A-8B depict examples where data from desired sources (e.g. data source 120 and 124) are extracted and then attached to distributed data objects to generate data source objects, in other examples a multidimensional data set comprising a plurality of data from one or more data sources may first be generated, and this multidimensional data set may then be attached to a distributed data object to generate the desired data source object. Accordingly, turning to FIG. 9, an example illustration 900 is depicted, showing an example multidimensional data set 900 for a particular patient. In this example illustration of a multidimensional data set 900, it may be understood that the particular patient includes patient 804, described above with regard to FIG. 8A. Dimensions of the multidimensional data object are depicted as a Cartesian coordinate system 905. The x-axis of the multidimensional data set 900 includes biomedical information (e.g. 103) corresponding to patient 804; the y-axis of the multidimensional data set 900 includes data source information (e.g. what data source the medically-relevant information has been retrieved from); and the z-axis corresponds to time/date of particular year(s). As an example, consider scan data source 124, which, as discussed above, stores scan data. The scan data may include, but is not limited to, Mill data, CT data, and/or PET data. In this example, patient 804 is depicted as having Mill scans on January, 2012, May, 2013, and February, 2014. Patient 804 additionally is depicted as having CT scans on January, 2013, June, 2013, and April, 2014. Still further, patient 804 is depicted as having PET scans on March, 2011, and April, 2014. As another example, consider genomics file system 120, which as discussed above stores genomic data. The genomic data may include, but is not limited to, whole or partial genomic sequence data, transcriptomic data, and/or targeted panels. While not explicitly illustrated, various genomic data may have been acquired at various dates. For brevity, the scan data and the genomic data are included and the biomedical information is not illustrated for each additional data source or device on which the data source is located, but it may be understood that the multidimensional data set may include such information. In this way, a multidimensional data set may be created for an individual patient. While not explicitly illustrated, it may be understood that, along similar lines as that of FIG. 8A-8B, the multidimensional data set may be generated via a plurality of data source-specific schema as defined by the data integration schema as a function of specified integrity constraints. The multidimensional data set may be attached to a distributed data object to generate a data source object which, as discussed above, is defined as a distributed data set with data source specific schema that has been loaded from one or more data sources. Computations/analytics may then be performed on such a data source object, or in other examples the data source object for a particular patient may be joined or combined into a data pool that includes other similar data source objects generated for one or more other patients. In this way, computations/analytics may be conducted across a plurality of patients.

Figure 10:
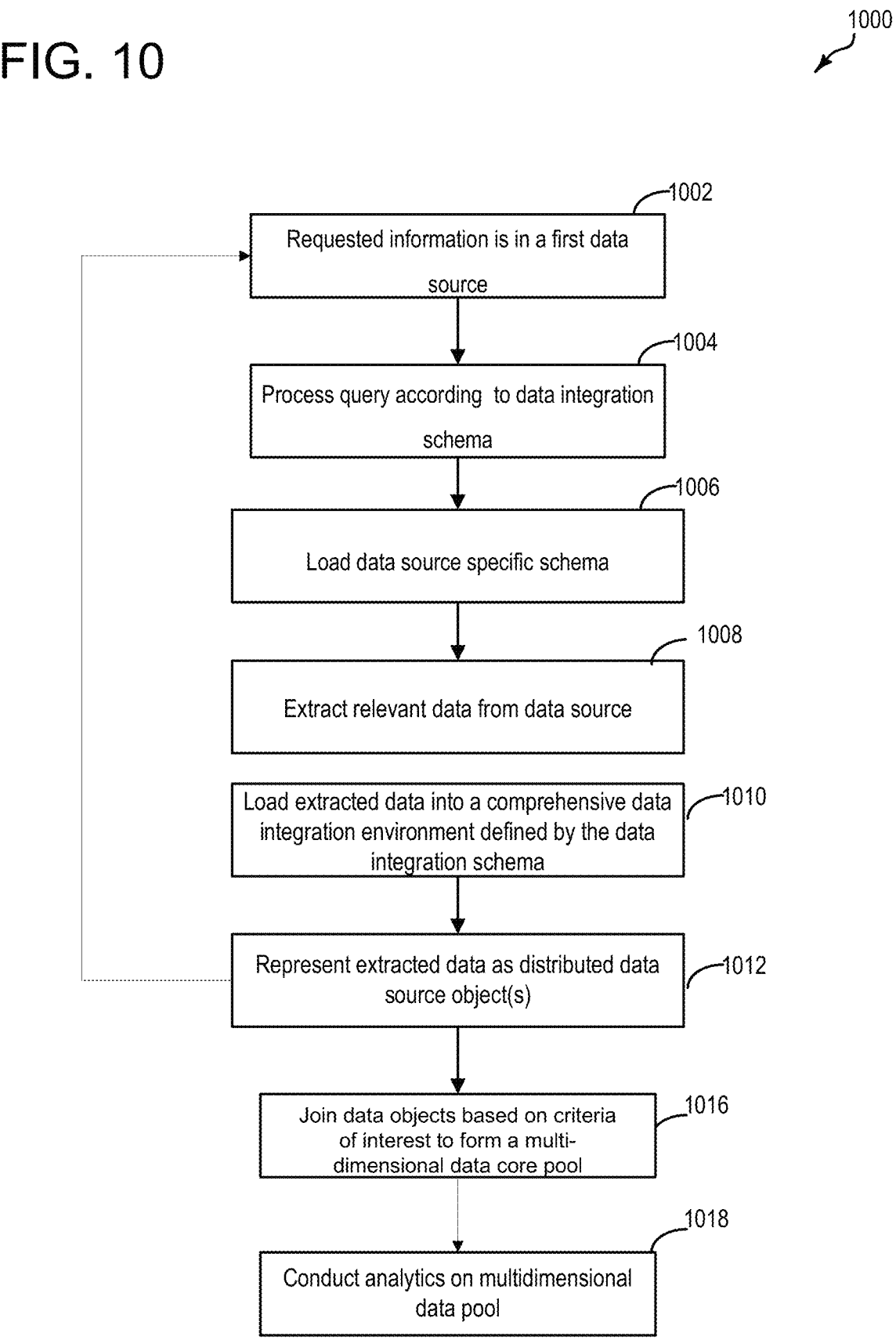
FIG. 10 depicts an example method for conducting a query.

Turning to FIG. 10, an example method 1000 of creating data pools and running analyses is shown. Specifically, a query request includes information that may be extracted from one or more data sources identified at 1002. The query is transformed using a data integration schema and the relevant data sources and information needed from the data sources is identified at 1004. For example, for a particular patient, an application suite of query and mining tools may be utilized to obtain the basic health record for such a patient, where data resides in a data source such as an Electronic Health Records database within a silo, such as records of a specific department. Such a process may be carried out for any number of patients. The specific schema relevant for the data source is selected at 1006 and the data is imported from the data source at 1008 and loaded into a comprehensive data integration environment defined by the data integration schema. The extracted data in the data integration schema format is represented as a data source object at 1012. The process may be repeated for multiple patients, and/or for multiple records for a single patient. As discussed above, the biomedical data may be stored in silos. Biomedically relevant scan data may include, but is not limited to, MRI images, PET scans, CT scans, etc. In such an example, the MRI images may be obtained via open-source applications from their respective data sources (e.g., scan data source), and the MRI images may be attached to a single distributed data object. As another example, the PET scan data for the same patient may be obtained, and the PET scan data may then be attached to a distributed data object. In other words, each type of data may be obtained and attached to a single distributed object or set of distributed objects. For the same patient, other biomedical data may be obtained from another data source located on the same or different devices as well. Consider the same patient, where various types of genomic data may be obtained from genomics database, or TileDB. Various types of genomic data may include whole genome sequencing results, transcriptomics data, targeted panel data, variants, etc. In such an example, the whole genome sequencing results may be attached to a single distributed data object or a set of distributed data objects. Represented data objects from one or more data sources are joined based on criteria of interest to form a multi-dimensional data pool at 1016. Analysis is then conducted on the multidimensional data core pool at 1018 and the response to the query returned. In some aspects, the data pool may be accessed via one or more APIs as discussed above in reference to FIG. 8.

Thus, information from disparate data types may be joined together in response to a query from a user. For instance, a user may want an answer that includes genomic variant data and clinical data based on a patient identifier or other integrity constraint as defined by the data integration schema. After joining into a data pool, the results are grouped by clinical label and a genomic aggregate calculation, such as genotype distribution, is calculated for each of the genomic variants for each clinical label category.

Using disparate sources of clinical data from different hospital systems does not change the structure of the resulting harmonized distributed data set from the user perspective if a new clinical data sources is added to the query. This allows for solving an N+1 problem by incorporating additional data into the data pools. In this way the data may be persisted, where persisted refers to methodology for storing data structures such that they can continue to be accessed using memory instructions or memory APIs even after the process that created or last modified them. In other words, creation of the data pools enables the data to be persisted. Accordingly, the above-described processes enable a clear way to store incoming data in their own silos, and enable a user to operate them using the current and legacy (e.g., old applications, computer systems, etc. tools). In this way, the N+1 problem may be solved using the methodology described herein, including the use of multidimensional data objects and sets.

It may be understood that, in the examples described above, processing of data may be done on either the various DBs/filesystems alone (e.g., 118, 120, 122, 124, 126, 128, 130) that are created via legacy tools, using an API associated with such legacy tools. Alternatively, processing may be done on the data stored in the data pool using the distributed data objects/sets (e.g., RDDs). By utilizing distributed data sets, programs and applications may not access just one type of data, but may process multiple types of data together. Such potential for processing multiple types of data together represents a clear advantage to the data core pool(s) discussed herein and the grouping of distributed data objects/sets, as doing so may result in higher performance, and enables users to exploit parallelism through a function such as map reduce.

Figure 11A:
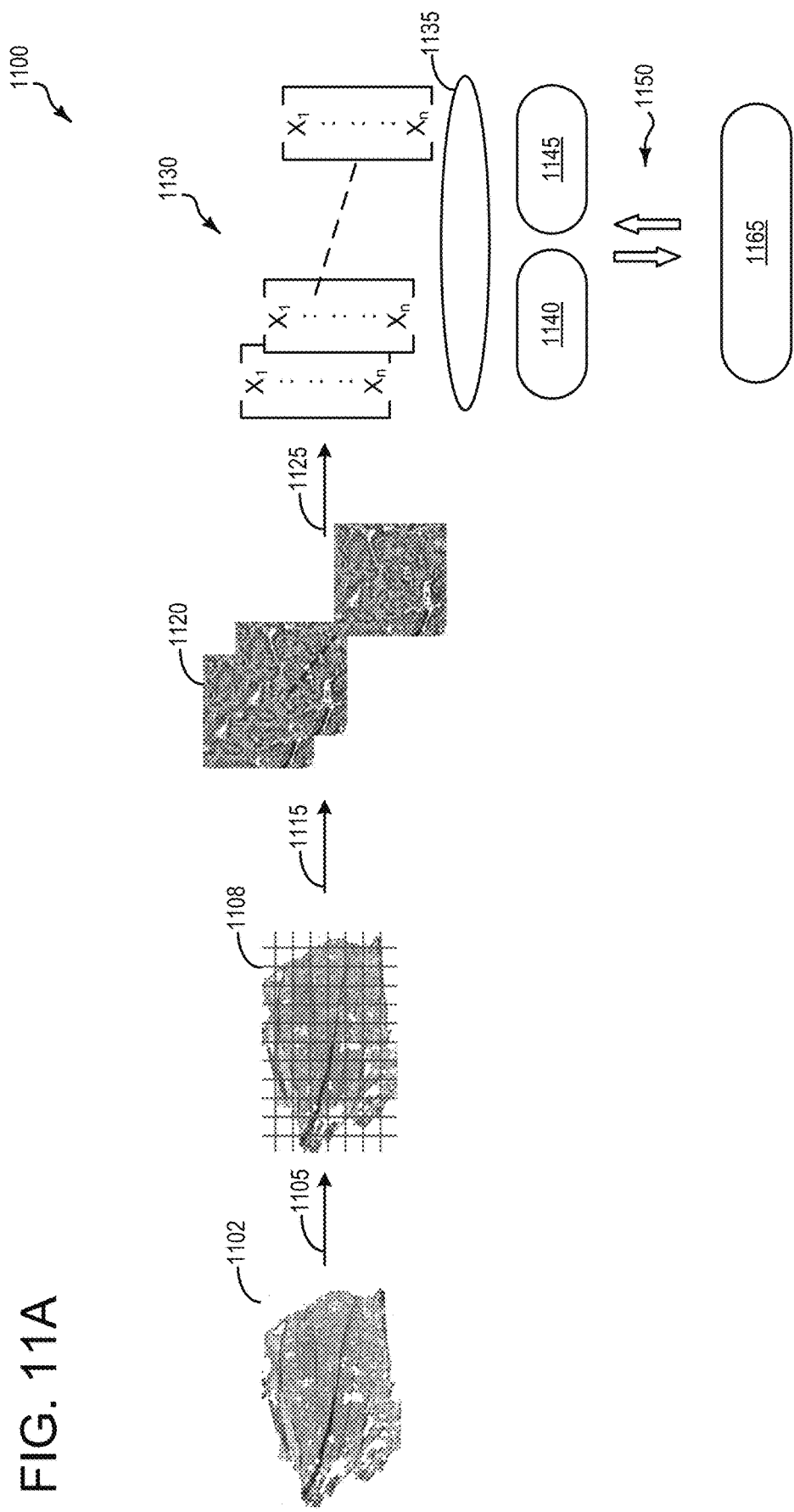
FIG. 11A is an example illustration of machine learning in an embodiment of a data core pool, such as the data pool depicted at FIG. 8A.

Turning to FIG. 11A, an example illustration 1100 of machine learning in a data pool is shown. Specifically, illustration 1100 includes a single image 1102. Image 1102 may be understood to comprise an image of tissue from a patient (e.g., 804). Such an image may comprise biomedical data (e.g., 103), which along with other biomedical data may be included in a data source object. Such a data source object may be incorporated into a data pool. For clarity, a single image is shown, but it may be understood that any data pool may include any number of images, as well as other medically-relevant data.

As an example of the types of analytics that may be conducted on data pools, a tiling operation 1105 may be conducted on image 1102 (and other images in the data pool), in order to transform the image 1102 into a plurality of smaller images 1108, or tiles, that together, represent the whole image 1102. The tiles may be processed 1115 for particular features, to yield processed tiles 1120. Particular features may include medically-relevant features, such as indications of a tumor or tumors, for example. In another example, such a feature may comprise a particular density of blood vessels, abnormal discoloration, etc. More specifically, in machine learning and pattern recognition, a feature may comprise an individual measurable property or characteristic of something being observed. Determining relevant features of a particular image, for example, may comprise a crucial step towards facilitating the use of algorithms comprising pattern recognition, classification, and regression. In some examples, extracting or selecting particular features may include predefined feature characteristics, and may include some aspect of feature learning itself. In other words, in some examples, identified features may comprise learned features, where such features may subsequently be used in downstream machine learning applications.

Features may be represented as numeric in some examples, but may be represented structurally (e.g., strings and/or graphs) in other examples. As an example, a particular feature or features may be described via a feature vector or vectors. Such feature vector(s) may be processed as feature workflows 1125. Accordingly, a data pool (e.g., 878, 896) may include a number of feature vectors 1130, which may correspond to particular features of related tissue images from various patients. In order to conduct machine learning on such features, machine learning applications may be customized via an application programming interface 1135, to enable deep learning 1140 and/or machine learning analytics 1145. Deep learning 1140 and/or machine learning analytics 1145 may include classification and/or prediction 1150 of various features, for example. Classification may be understood to comprise a family of machine learning algorithms that may identify which category an item belongs to. As one relevant example, classification of particular features of tissue samples from one or more individual patients may include an indication of whether a particular tissue comprises a malignant cancer tissue or not. Classification as described in relation to machine learning may thus include taking a set of data with known labels (e.g., malignant) and predetermined features (e.g., cell size, cell shape, cell uniformity, etc.), and then learning/predicting whether other particular set(s) of data include similar features, such that said other particular set(s) of data may be similarly labeled or not. In another example, machine learning and/or deep learning may be utilized to predict a probability, which may then be used to predict a particular feature. As an example, a logistic regression method may be utilized to predict a binary response. Referring to example illustration 1100, particular features of the tissue image (e.g., 1102) may include cell clump thickness, uniformity of cell size, uniformity of cell shape, adhesion qualities, bare nuclei, bland chromatin, etc. Based on the particular features, machine learning may produce probabilities or predictions that a particular tissue from a particular individual or individuals comprises a malignant tissue sample. In other words, machine learning and/or deep learning may allow for classification and/or prediction strategies, thus enabling automated annotation 1165 of all data stored in the data pool.

While the above-described illustration 1100 depicts a tissue image, it may be understood that such an example is meant to be illustrative. In other examples, machine learning strategies may be conducted on a data pool (e.g., 879 or 896) to classify and/or predict susceptibility to particular diseases, based on genetic information. For example, genomic sequencing data may be acquired from various individual patients, and may be incorporated into a data pool as described above. Machine learning operations may be conducted on the genomic sequencing data from the various individuals, to predict what individuals may be susceptible to a particular type of cancer, for example. In another example, machine learning may be conducted to classify particular individuals as a function of genomic sequencing data. For example, classification in such a context may include classifying particular individuals as being highly likely to achieve favorable or desirable results from a particular type of treatment, based on machine learning of genomic sequence data and relevant treatment outcomes. In still other examples, more than one type of medically-relevant data set may be operated on in parallel via machine learning techniques, to uncover novel biological insights that would not be possible if the current methodology were not utilized, due to exponential computational run-time as the types of data to be analyzed together increases.

As mentioned, the above-described examples of machine learning techniques are meant to be illustrative. In other words, a particular advantage to pooling data source objects into a data pool is that machine learning may be applied to any and all medically-relevant data, for particular individuals and across individuals. The distributed nature of the data source objects comprising the data pool may allow for parallel processing of particular queries that involve machine learning and automated data annotation, which may cut down substantially on computational run-time to produce a desired output. In other words, the systems and methods described herein may allow for large scale analytics to be conducted on medically-relevant data from individual patients and across patients, which may allow for personalized medical diagnosis, treatment options, etc.

Figure 11B:
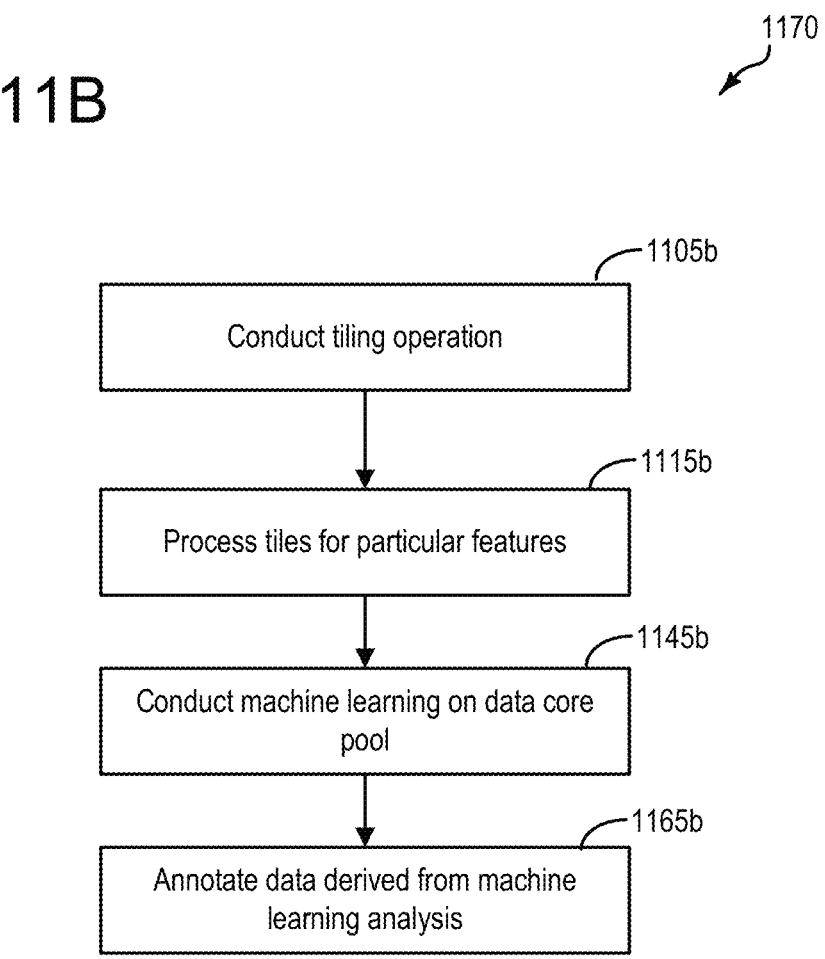
FIG. 11B is a flowchart illustrating an example of machine learning in an embodiment of a data pool, such as the data pools depicted at FIG. 8.

Turning to FIG. 11B, a high-level example method 1170 is shown, depicting the process flow illustrated at FIG. 11A. Like numerals between FIGS. 11A and 11B are referred to by the same numeral, but with the numerals containing a "b" for FIG. 11B. As the description for FIG. 11B is substantially similar to the process flow of FIG. 11A, the various steps will be mentioned briefly, and for further detail, refer to FIG. 11A.

Accordingly, a tiling operation is first conducted at 1105b on an image or plurality of images, as discussed. Subsequently, at 1115b, the tiles may be processed for particular features. As discussed, a particular feature or features may be described via a feature vector or vectors, and may be processed as feature workflows (e.g., 1125).

Proceeding to 1145b, method 1170 may include conducting machine learning on features in a data pool (see FIGS. 8A-8B). More specifically, deep learning (e.g., 1140) and/or machine learning may include classification and/or prediction of various features, as discussed in detail above.

Subsequent to the machine learning step at 1145b, method 1170 may proceed to 1165b. At 1165b, method 1170 may include annotating data derived from machine learning analysis at 1145b. Any type of data may be used to create machine learning inferences through a matrix.

Figure 12:
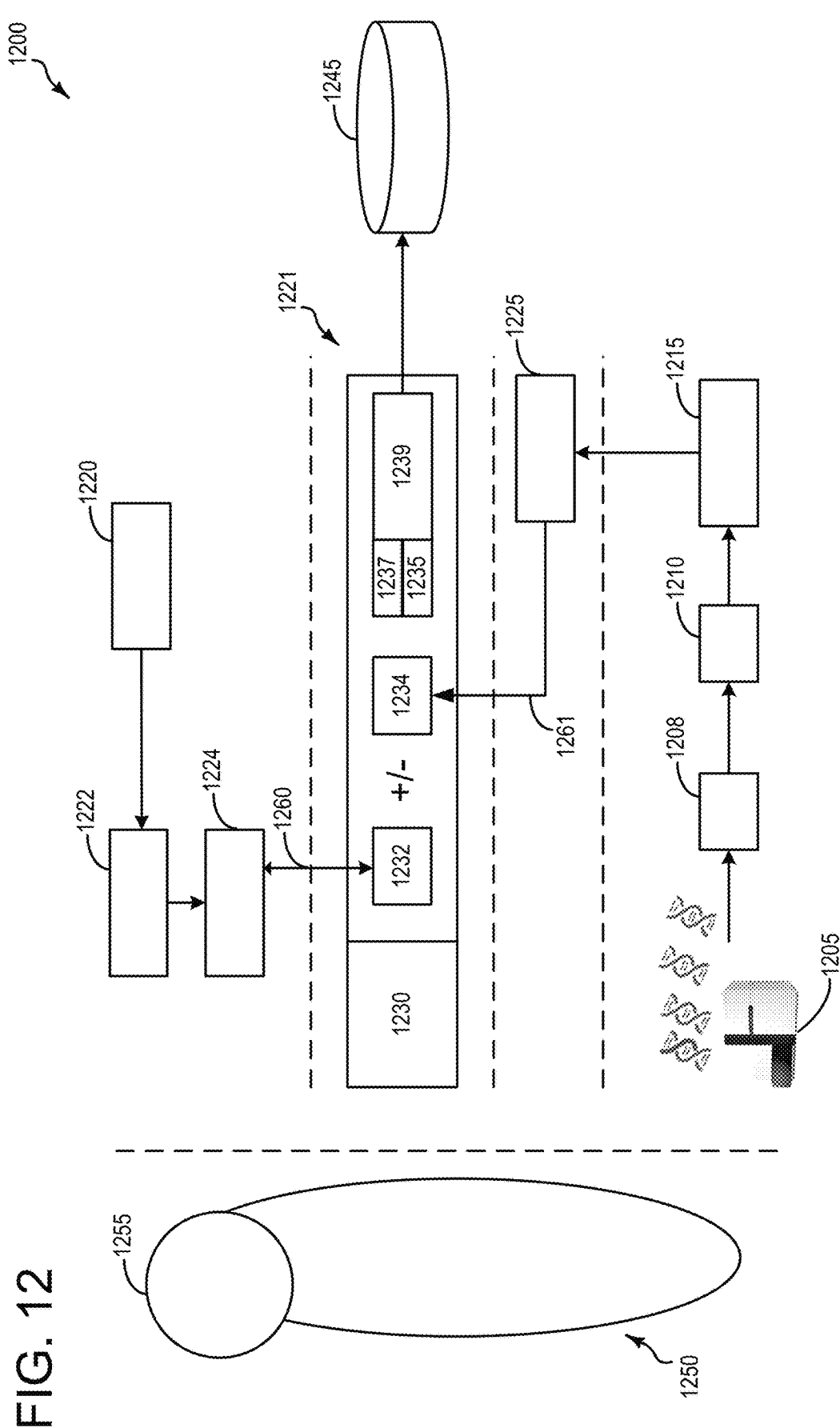
FIG. 12 is an example illustration of design and implementation details for carrying out the methodology discussed above at FIG. 3, FIG. 10, and FIG. 11B.

Turning now to FIG. 12, an example illustration 1200 is shown, depicting the overall design details of how particular cohorts may be generated according to the methodology described herein. Specifically, FIG. 12 illustrates how multiple types of data (e.g., siloed medical data) may be combined, how data may then be analyzed (e.g., using machine learning algorithms (e.g. MLLib and/or GraphX), and how cohorts may be created. For simplification of the description of FIG. 12, the types of data are restricted to genomic data and clinical data (e.g., electronic health record), but it may be understood that such an example is meant to be illustrative and that the process flow of FIG. 12 may be extended to any number of data types for a particular individual and/or across individuals.

Accordingly, FIG. 12 depicts process flow for a user-defined query. The query is entered into a client device 1250 that may include a notebook interface 1255 such as Apache Zepplin that is used to take inputs from different data sources and integrate and analyze them to produce the answer to the user defined query. For example, particular data source(s) may be the only source for answering the user-defined query. In other aspects, multiple data sources may contain the information useful in answering the user-defined query. Using a data integration schema, the query is translated to a cohesive query identifying the databases and information needed to provide the desired results. In this example, information from an EHR 1220 and GenomicsDB 1215 are used to provide the requested results and the query is parsed into query segments as a clinical cohort query 1232 and a genomics cohort query 1234 to allow for interfacing with the two different data sources. The resulting information gathered from those two queries will be combined and analyzed to generate the desired result. Though two databases and query segments are shown, there may be three, four, five, six, seven, eight or more query segments that may be created and data bases accessed as determined by the conversion of the user-entered query to a cohesive query.

Information in the databases 1220 and 1215 may be produced and stored in any manner generally used. In this example, a tissue sample is sequenced 1205 and the resulting data is stored as generated variant call format (VCF) files 1208. Such files may be processed, for example via python scripts 1210, for storage at GenomicsDB 1215 (e.g., genomics file system 120 of FIG. 1). Along similar lines, clinical data 1220 (e.g. electronic health record) from any number of patients may be processed via application tools 1222, for storage at a common relational data source 1224 (e.g. an object-relational database management system with an emphasis on extensibility and standards compliance such as PostgreSQL).

The query segments use data source specific schema to access the information pertaining to the query segment from the data source. The data source specific schema comprises integrity constraints relevant to the structure of the associated data source. For example, for a first data source-specific schema 1260, the associated integrity constraints, provide the structure used to extract the desired set of data from relational data source 1224 at the data integration layer 1221. A first query segment may be clinical cohort query 1232 which may be used to retrieve or trigger retrieval of a desired set of data from relational data source 1224. For a second data source-specific schema 1261, the associated integrity constraints provide the structure used to translate a second query segment to extract the desired set of data from the genomics data source 1215. In this example second data source-specific schema 1261 comprises at least in part a genomics data source API 1225 for extracting the desired set of data from genomics data source 1215.

The extracted data from each of the relational data source 1224 and the genomics data source 1215 may then be translated back through the data source-specific schema, thereby, generating data that maps to a data integration schema. The generated data may be attached to one or more distributed data objects 1230 to generate data source objects (not specifically depicted at FIG. 12) comprising one or more distributed data sets with data loaded from the specified data sources (e.g., 1224 and 1215). It may be understood that the data source objects are distributed across any number of machines for parallel processing in a fault-tolerant manner.

Such a system may enable machine learning approaches for uncovering novel biological insights from the data, generation of particular cohorts, etc. Machine learning approaches may comprise use of a machine learning library 1237 (e.g., MLLib) as one example, and may include use of an API (e.g., GraphX) 1235, for graph creation and graph-parallel computation methodology. In some examples, custom machine learning algorithms 1239 may be utilized for particular machine learning approaches. Insights learned from such approaches may be processed and stored in high performance file system(s) 1245 and/or returned to client devices 1250.

For example, a user-entered query may be translated into an SQL query for a relational database and a list of named column intervals (e.g., chromosomes, genes, etc.) for use with GenomicsDB. The SQL query may be used to access the relational database which outputs a table comprising rows including samples and columns including phenotype data. The rows of samples are converted to a list which is used in conjunction with the list of named column intervals to access the GenomicsDB which then outputs a matrix comprising rows of samples and columns of variants attached to distributed data objects. The output of the relational database (matrix of samples and phenotype data) and the output of GenomicsDB (matrix of samples and variants) are then combined to form a matrix of rows of samples and columns with phenotype, genotype data as a dense array upon which operations can be exercised.

Figure 13:
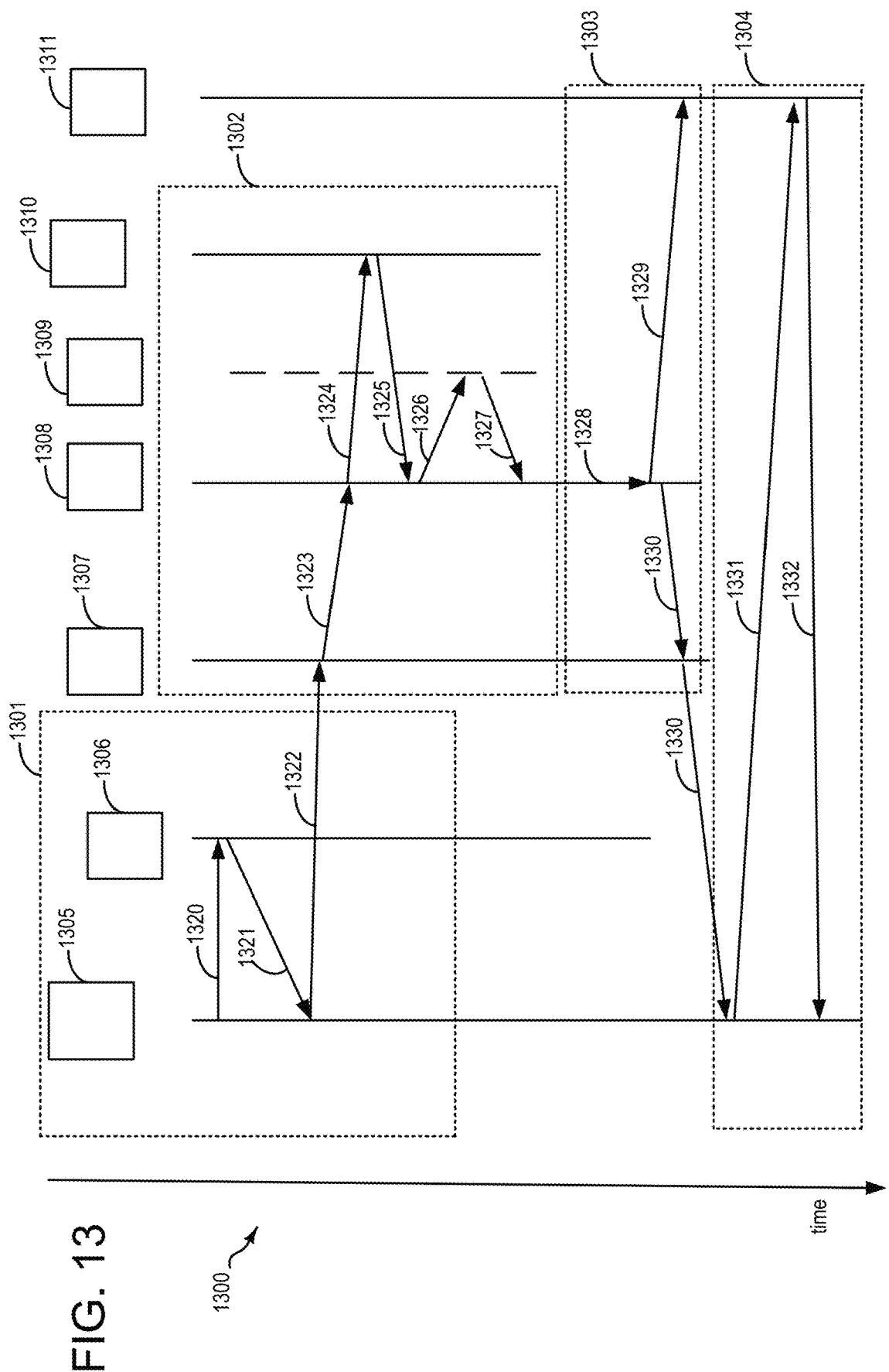
FIG. 13 is a particular example illustration of how a query is conducted, using the systems and methods of the present disclosure.

Turning now to FIG. 13, a high level example illustration 1300 is depicted, illustrating how the methods and systems described above may be implemented in server clusters, or in a cloud environment (e.g., Amazon web services in a HIPPA certified environment). Specifically, example illustration 1300 depicts how the system works when a user creates cohorts with interspersed query from both a patients electronic health record (EHR) and "variants" from genomics database. In example illustration 1300, time flows from top to bottom of the illustration, as depicted, and the various arrows depict control flow between software modules and various data sources. Specifically, example illustration 1300 depicts a processing of a query, which uses an application and plugin 1305, relational database (RDB) 1306, elastic map reduce (EMR) and data source such as genomics DB (GDB)/data analytics cluster computing client 1307, GDB/data analytics cluster computing secondaries 1308, storage (GDB mount) 1309, ID mapping server 1310, and non-relational database 1311. The various steps illustrated at FIG. 13 are depicted as four high level steps. Specifically, first step 1301 is followed by second step 1302, which is followed by third step 1303, which is then followed by fourth step 1304. It may be understood that illustration 1300 does not depict how data sources on any one device are created.

In the first step 1301, a user makes a query through the plugin 1305, using for example, SQL 1320. In such an example, the query may include one or more of diagnosis, symptomology, demographic, and/or other biomedical data that may be included in an electronic health record (EHR). The user-defined query may further include one or more other medically-relevant data, such as genomic data, image data, scan data, etc. or patient specific data such as a patient name.

Desired patient and clinical attributes, or EHR info 1321 defined by the SQL query 1320 is then retrieved from RDB 1306. The plugin 1305 then submits a data analysis cluster computing job 1322 with the EHR info and requested analysis from the user.

In the second step 1302, data analysis cluster computing client 1307 delegates secondaries 1308 via a cryptographic network protocol for operating network services securely over a network, for example via a security protocol such as secure shell (SSH) 1323. Secondaries 1308 then query the ID mapping server 1310 via a standard language for storing, manipulating, and retrieving data in databases, such as SQL 1324. For example, if the query included a request for particular genomic data, then the mapping information may include mapping information related to the genomic DB. In another example, if the query included a request for particular scan data, then the mapping information may include mapping information related to the scan data source (e.g., PACS DB). In still another example, if the query included a request for particular image data, then the mapping information may include mapping information related to the image data source (e.g., Omero). In some examples, a query may include a request for more than one other type of medically-relevant data, such as image data and scan data, for example, at which point mapping information related to both databases may be retrieved.

In this example illustration 1300, the SQL query 1324 is translated through the data integration schema into a cohesive query and query segments are used to retrieve GDB mapping info 1325. Mapping info 1325 is then used to query the GDB via, for example via programming framework 1326 specific to GDB (data source specific schema), in order to load GDB variants 1327 into distributed objects. In the third step 1303, user-defined analysis 1328 is performed in a data analysis cluster computing tool, and the results are written 1329 (e.g., https) to a non-relational database 1311 as an aggregated set. It may be understood that the data that is written at 1329 is dependent upon what the user-defined analysis 1328 produces. When the analysis is finished, a success return code 1330 signals to the plugin 1305.

In the fourth step 1304, the return code 1330 signals the plugin 1305 to read 1331 (e.g., https) finished results from the non-relational database 1311. Results are returned 1332 to the web client plugin 1305 via standard http communication, for example.

While example illustrations 1200 and 1300 depict a situation where a user is interested in generating a particular cohort based on EHR data and genomic data, it may be understood that such a query is not limited to generating cohorts based on EHR data and genomic data, but may instead be applied to any type of biomedical data from any number of data sources, as discussed above. For example, a user may want to generate a cohort based on EHR data and scan data. In another example, a user may want to generate a cohort based on EHR data and image data. In other examples, a user may want to generate a cohort based on EHR data and more than one other type of biomedical data, for example scan data and image data, or scan data, image data, and genomic data or combinations of data not including HER data. As described above, if the systems and methodology discussed herein were not implemented, such queries involving more than one type of biomedical data may be performed serially, thus limiting usefulness of such an approach due to prohibitive computational run times. However, by implementing the above-described systems and methodology, generation of user-defined cohorts based on a plurality of different types of medically-relevant data obtained from patients, may be readily accomplished as shown in FIGS. 3 and 10.

While methods for integrating a plurality of medical data for one or more individuals from a variety of data sources may be run, serially, in parallel, or through a distributed computing system, in some embodiments, a distributed computing system may be used.

Figure 14:
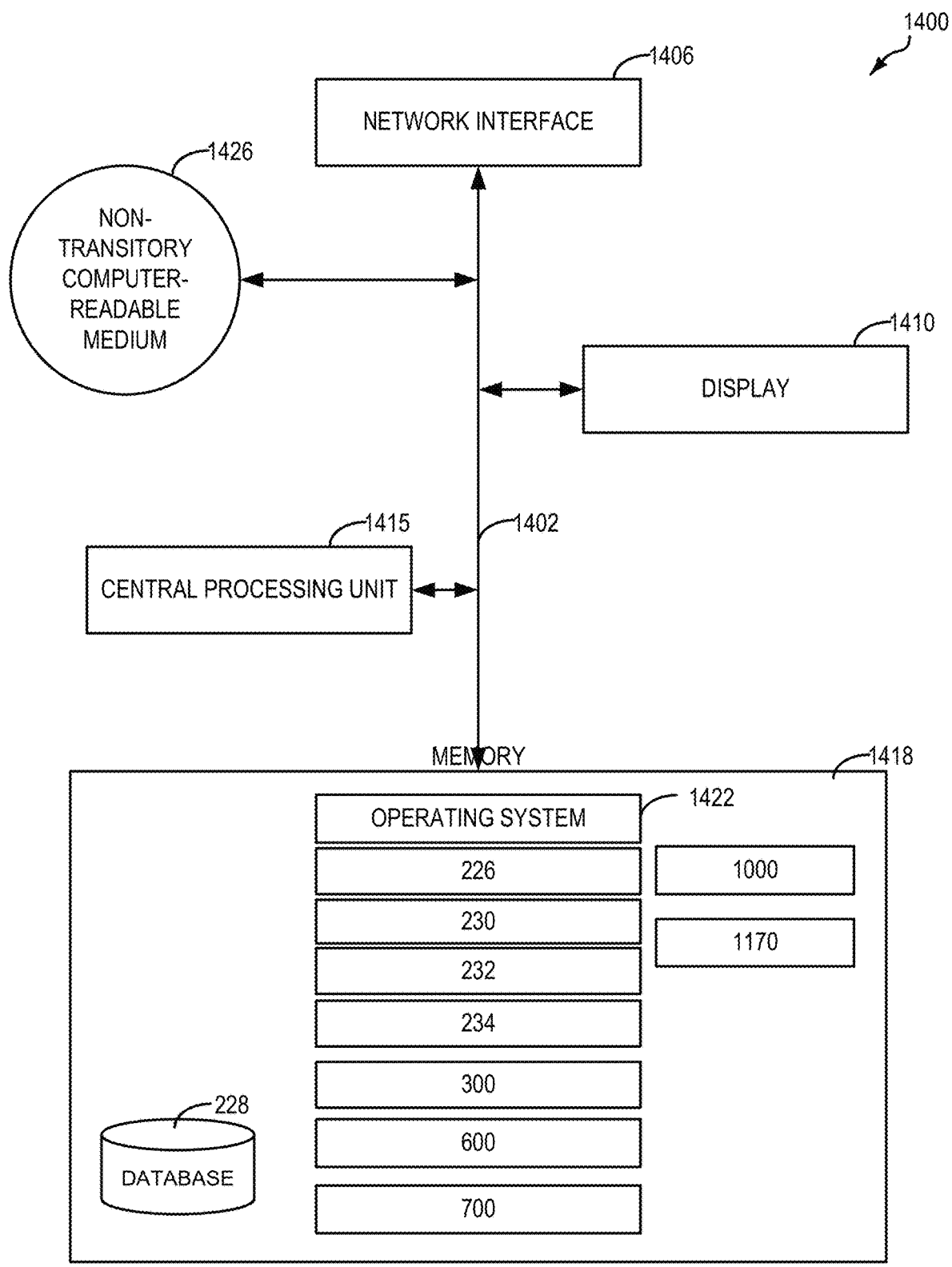
FIG. 14 illustrates a system in accordance with an embodiment described herein.

FIG. 14 illustrates several components of an exemplary system 1400 in accordance with an embodiment of the present disclosure. In various embodiments, system 1400 may include a desktop PC, server, workstation, mobile phone, laptop, tablet, set-top box, appliance, or other computing device that is capable of performing operations such as those described herein. In some embodiments, system 1400 may include many more components that those shown in FIG. 14. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware. In some aspects, logic and memory may be integrated into one or more common devices, such as an application specific integrated circuit or a system on a chip.

In various embodiments, system 1400 may comprise one or more physical and/or logical devices that collectively provide the functionalities described herein. In some embodiments, system 1400 includes a bus 1402 interconnecting several components including a network interface 1406, a display 1410, a central processing unit (CPU) 1414, a memory 1418, and a communication subsystem 1420.

System 1400 may be configured to execute one or more instructions that are part of one or more applications, services, programs, routines, libraries, objects, components, data structures, or other logical constructions. Such instructions may be implemented to perform a task, implement a data type, transform the state of one or more devices, or otherwise arrive at a desired result. System 1400 may include one or more processors that are configured to execute software instructions. Additionally or alternatively, the logic subsystem may include one or more hardware or firmware logic machines configured to execute hardware or firmware instructions.

Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

In some embodiments, system 1400 may comprise one or more computing resources provisioned from a "cloud computing" provider. "Cloud computing" or of/in "the Cloud" as used herein refers to a model for enabling ubiquitous, convenient, on-demand network access to a shared pool of configurable computing resources that can be rapidly provisioned and released with minimal management effort or service provider interaction." The defined model comprises five characteristics, which are on-demand self-service, broad network access, resource pooling, rapid elasticity, and measured service. (The NIST Definition of Cloud Computing (NIST Special Publication 800-145)). Clouds can be private, hybrid, or public, and may include Infrastructure as a Service (IaaS), Platform as a Service (PaaS) and Software as a Service (SaaS).

Cloud computing providers include, for example, Amazon Elastic Compute cloud ("Amazon EC2"), provided by Amazon.com, Inc. of Seattle, Wash.; Sun cloud Compute Utility, provided by Sun Microsystems, Inc. of Santa Clara, Calif.; Windows Azure, provided by Microsoft Corporation of Redmond, Wash., and the like.

Display 1410 may be used to present a visual representation of data held within memory 1418 or database 228. As the herein described methods and processes change the data held in the memory 1418 or database 228, the state of the information displayed may also change. For example, display 1410 may be used to present a visual representation of data using, for example, a "Graphics processing unit" (GPU), a processing unit that comprises a programmable logic chip (processor) specialized for display functions. The GPU may render images, animations, and video for a computer screen. The GPU may be located on plug-in cards, in a chipset of a motherboard of a computer, or in the same chip as the central processing unit (CPU). The GPU may perform parallel operations on multiple sets of data, and thus may be used as vector processors for non-graphics applications which involve repetitive computations.

Memory 1418 generally comprises a random access memory ("RAM") and permanent non-transitory mass storage device, such as a hard disk drive or solid-state drive. Memory 1418 stores an operating system 1422 as well as processes 226, 230, 232, 234, 300, 600, 700, 1000, 1170. Software components may be loaded into memory 1418 of system 1400 using a drive mechanism (not shown) associated with a non-transitory computer-readable medium 1426, such as optical memory (for example CD, DVD, HD-DVD, Blu-Ray Disc, memory stick, and the like) and/or magnetic memory devices (for example hard disk drive, floppy disk drive, tape drive, MRAM, and the like). It may further include devices which are one or more of volatile, non-volatile, dynamic, static, read/write, read-only, random access, sequential access, location addressable, file addressable and content addressable.

Memory 1418 also may include database 228. In some embodiments, system 1400 may communicate with database 228 via network interface 1406, a storage area network ("SAN"), a high-speed serial bus, and/or via any other suitable communication technology. By way of example, such architectures include Micro Channel Architecture (MCA) bus, Enhanced ISA (EISA) bus, VESA Local Bus (VLB), and Peripheral Component Interconnects (PCI) bus.

In some embodiments, database 228 may comprise one or more storage resources provisioned from a "cloud storage" provider, for example Amazon Simple Storage Service ("Amazon S3"), provided by Amazon.com, Inc. of Seattle, Wash., Google cloud Storage, provided by Google, Inc. of Mountain View, Calif., and the like. In some embodiments, such databases may be compliant with HIPPA or other government regulatory requirements.

Communication subsystem 1420 may be configured to communicatively couple system 1500 with one or more other computing devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like. Aspects of the present disclosure are described herein with reference to flowchart illustrations and/or block diagrams of methods, apparatus, and computer program products according to the embodiments disclosed herein. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram blocks.

The description of embodiments has been presented for purposes of illustration and description. Suitable modifications and variations to the embodiments may be performed in light of the above description or may be acquired from practicing the methods. For example, unless otherwise noted, one or more of the described methods may be performed by a suitable device and/or combination of devices, such as the integration server or client devices of FIG. 2, etc. The described methods and associated actions may also be performed in various orders in addition to the order described in this application, in parallel, and/or simultaneously. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

For purposes of illustration, specific data sources such as GenomicsDB have been used. However, this is not intended as a limitation on the scope of the present disclosure. The embodiments of the present disclosure may be applied to any other document source such as VCF files, CSV files, other flat files such as TIFF, BAM, image files, text files and the like. In some examples, the other document source may comprise traditional SQL databases. The term "document" generally refers to a document or record and its associated data within a data source. Such documents may be in structured or unstructured formats. In some examples a "document" may be any object that includes or contains a list of key-value pairs, wherein each key is a string and the value is either another object, an array (that is, a list of objects) or a simple value that may be a string or a number. In other aspects the document may refer to an unstructured file object, such as a text of binary encoded file.

Those skilled in the art will recognize that optical aspects of implementations may involve optically-oriented hardware, software, and or firmware. The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs, semiconductor devices based around a matrix of configurable logic blocks (CLBs), connected via programmable interconnects. FPGAs as discussed in this context can be reprogrammed to desired application or functionality requirements after manufacturing), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

For example, in some examples, a device such as a computer comprising a compute node may include a processor component and a storage to store instructions that, when executed by the processor component may cause the processor component to retrieve, from one or more storage devices through a network, metadata indicative of organization of data within a data set, map data indicative of organization of multiple data blocks within a data file maintained by the one or more storage devices, wherein the map data may include multiple data blocks within a data file maintained by the one or more storage devices, or wherein the map data includes multiple map entries corresponding to one or more data blocks of the multiple data blocks; and receive, from multiple node devices, indications of which node devices among the multiple node devices are available node devices that are each able to perform a processing task with at least one data set portion of the one or more data set portions.

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

The foregoing described aspects depict different components contained within, or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

The invention claimed is:

1. Method for distributed compilation and joint analysis of data from multiple biomedical sources, the method being implemented by a computer system comprising one or more processors executing computer program instructions that, when executed, perform the method, the method comprising:
   receiving, at an integration server configured with a data integration specification and adapted to service requests from a client device, a query from the client device requesting analysis of one or more types of biomedical data;
   storing, in a memory of the computer system, a data integration schema and integrity constraints, wherein the integration server is part of the computing system;
   mapping the query with respect to the data integration schema and integrity constraints, wherein the data integration schema identifies sources of information usable for answering the query;
   storing, in the memory of the computer system, data source specific schema;
   retrieving a first instance of biomedical data from at least one data source based on a first data source specific schema of the stored data source specific schema;
   mapping the first instance of biomedical data from at least one data source to the data integration schema;
   generating a first data source object by attaching the retrieved first instance of biomedical data from at least one data source to a first distributed data object;
   conducting a first computation within the first data source object and generating a third data source object based on the first computation;
   retrieving a second instance of biomedical data from the at least one data source based on a second data source specific schema of the stored data source specific schema;
   mapping the second instance of biomedical data from the at least one data source to the data integration schema;
   generating a second data source object by attaching the retrieved second instance of biomedical data from the at least one data source to a second distributed data object;
   conducting a second computation within the second data source object and generating a fourth data source object based on the second computation;
   combining the first data source object, the second data source object, the third data source object, and the fourth data source object to form a multidimensional data pool;
   processing an operation corresponding to the query within the multidimensional data pool to generate a response to the query; and
   returning the response to the query to the client device.

2. The method of claim 1, wherein the operation is data manipulation, mathematical or statistical operations.

3. The method of claim 1, wherein the first instance of biomedical data and the second instance of biomedical data are located in different data sources.

4. The method of claim 3, wherein the different data sources are in different data silos.

5. The method of claim 3, wherein the first instance of biomedical data and the second instance of biomedical data are associated with a same patient.

6. The method of claim 3, wherein the first instance of biomedical data and the second instance of biomedical data are associated with different patients.

7. The method of claim 1, wherein the first instance of biomedical data and the second instance of biomedical data are located in a same data source.

8. The method of claim 7, wherein the first instance of biomedical data and the second instance of biomedical data are associated with different patients.

9. The method of claim 1, wherein the first instance of biomedical data and the second instance of biomedical data comprise one or more forms of data,
   wherein the one or more forms of data are at least one of ASCII, JPEG, GIF, diagnostic imaging, FASTA, BED, 2 bit, GTF2, GFF3, PSL, BigBED, BedGraph, wiggle, BigWig, bowtie, SAM, PSL, BAM, HL7, X12, CCR, CCD, C32, CCDA, DICOM, TIFF, PNG, compressed files, ISO, SDI, database files, flat files, PDF, formatted text, plain text, and XML.

10. The method of claim 1, wherein the data pool is analyzed using machine learning to identify a plurality of similarly situated patients, or cohorts of similarly situated patients, as a function of the query.

11. The method of claim 10, wherein the similarly situated patients have one or more of a same health profile, a same genetic variant of a disease, a same phenotypic variant or a same epigenetic profile of the disease.

12. The method of claim 1, wherein the query is defined at least in part by one or more integrity constraints related to the query; and
   wherein the integrity constraints consistently return a same value for the query from different data sources representing a same data.

13. The method of claim 12, wherein the data integration schema ensures a same global representation of the same datatype extracted from the different data sources.

14. The method of claim 1, wherein after processing an operation corresponding to the query on the data pool to generate a response to the query, retrieving a third instance of biomedical data from the at least one data source based on the first or second data source specific schema of the stored data source specific schema;

mapping the third instance of biomedical data from the at least one data source to the data integration schema;

generating a fifth data source object by attaching the retrieved third instance of biomedical data from the at least one data source to a fifth distributed data object;

conducting computations on the fifth data source object; and combining the computations on the fifth data source object with the computations on the first data source object and the second data source object to return a response to the query.

15. A system for identifying cohorts of patients with related disease markers comprising:
   a processor;
   a storage device for storing a data integration specification and instructions executable by the processor to:
      receive queries from a client device and execute the queries, the client device comprising a computing device connected to an integration server via a network;
      store a data integration schema and integrity constraints comprising one or more data source specific schema for each of a plurality of data silos, wherein each data silo comprises biomedical data for a plurality of individuals; and
      extract one or more data sets from each of the plurality of data silos using the one or more data source specific schema;
      transform the data sets from the plurality of data silos into a plurality of data source objects, wherein each of the data source objects comprises a distributed data set with a particular data source-specific schema;
      conduct computations on each of the data source objects; and
      combine the computations to form a second data source object,
   wherein the plurality of data source objects and the second data source object are combined to form one or more multidimensional data pools.

16. The system of claim 15, wherein the plurality of data source objects are data source objects containing a same data type of biomedical data or different data types of biomedical data.

17. The system of claim 15, further comprising an interface whereby a user of the system for identifying cohorts of patients inputs a query into the client device that results in the generation of the one or more data source objects; and
   wherein the query is defined at least in part based on one or more integrity constraints related to the query.

18. The system of claim 17, wherein the integrity constraints consistently return a same value for a query from different data sources representing the same data.

19. A system for identifying cohorts of patients with related disease markers comprising:
   an input device;
   a processor; and
   a storage device for storing a data integration specification and instructions executable by the processor to:
      receive queries from the input device;
      execute the queries;
      store a data integration schema and integrity constraints comprising one or more data source specific schema for each of a plurality of data silos, wherein each data silo comprises biomedical data for a plurality of individuals; and
      extract one or more data sets from each of the plurality of data silos using the one or more data source specific schema;
      transform the data sets from the plurality of data silos into data source objects, wherein each of the data source objects comprises a distributed data set with a particular data source-specific schema;
      conducting computations on each of the data source objects; and
      combining the computations to form a second data source object,
   wherein the one or more data source objects and the second data source object are combined to form one or more multidimensional data pools.

20. The system of claim 19, wherein the queries are received by a query application executed on the system.

* * * * *